United States Patent
Andrei et al.

(10) Patent No.: US 11,040,047 B2
(45) Date of Patent: Jun. 22, 2021

(54) PRODRUGS OF NUCLEOSIDE PHOSPHONATES

(71) Applicant: Katholieke Universiteit Leuven, Leuven (BE)

(72) Inventors: Graciela Andrei, Leuven (BE); Steven De Jonghe, Leuven (BE); Elisabetta Groaz, Leuven (BE); Piet Herdewijn, Heverlee (BE); Min Luo, Leuven (BE); Dominique Schols, Leuven (BE); Robert Snoeck, Leuven (BE)

(73) Assignee: Katholieke Universiteit Leuven, Leuven (BE)

( * ) Notice: Subject to any disclaimer, the term of this patent is extended or adjusted under 35 U.S.C. 154(b) by 0 days.

(21) Appl. No.: 16/495,606

(22) PCT Filed: Mar. 21, 2018

(86) PCT No.: PCT/EP2018/057180
§ 371 (c)(1),
(2) Date: Sep. 19, 2019

(87) PCT Pub. No.: WO2018/172416
PCT Pub. Date: Sep. 27, 2018

(65) Prior Publication Data
US 2020/0016180 A1    Jan. 16, 2020

(30) Foreign Application Priority Data

Mar. 23, 2017  (GB) .................................... 1704577
Jul. 12, 2017   (GB) .................................... 1711193

(51) Int. Cl.
*A61K 31/675* (2006.01)
*A61P 31/22* (2006.01)
*C07F 9/6584* (2006.01)

(52) U.S. Cl.
CPC ............ *A61K 31/675* (2013.01); *A61P 31/22* (2018.01); *C07F 9/6584* (2013.01)

(58) Field of Classification Search
None
See application file for complete search history.

(56) References Cited

PUBLICATIONS

Hostetler et al. "Enhanced antiproliferative effects of alkoxyalkyl esters ofcidofovir in human cervical cancer cells in vitro" Molecular Cancer Therapeutics, 2006, vol. 5, No. 1, pp. 156-159.*
Keith et al., "Evaluation of Nucleoside Phosphonates and Their Analogs and Prodrugs for Inhibition of Orthopoxvirus Replication" Antimicrobial Agents and Chemotherapy (2003) 47(7):2193-2198.

International Search Report and Written Opinion dated Jul. 11, 2018 for PCT Application No. PCT/EP2018/057180, filed Mar. 21, 2018.
Bischofberger et al., "1-[((S)-2-Hydroxy-2-Oxo-1,4,2-Dioxaphosphorinan-5-yl)Methyl]Cytosine, an Intracellular Prodrug for (S)-1-(3-Hydroxy-2-Phosphonylmethoxypropyl)Cytosine with Improved Therapeutic Index in Vivo" Antimicrob. Agents Chemother. (1994) 38(10):2387-2391.
Campos et al., "Human cytomegalovirus antiviral drug resistance in hematopoietic stem cell transplantation: current state of the art" Rev. Med. Virol. (2016) 26:161-182.
De Clercq, E., "Antivirals for the treatment of herpesvirus infections" J. Antimicrob. Chemother. (1993) 32 (Suppl. A):121-132.
De Clercq, E., "Cidofovir in the treatment of poxvirus infections" Antiviral Research (2002) 55:1-13.
De Clercq, E., "Clinical Potential of the Acyclic Nucleoside Phosphonates Cidofovir, Adefovir, and Tenofovir in Treatment of DNA Virus and Retrovirus Infections" Clin. Microb. Rev. (2003) 16(4):569-596.
De Clercq et al., "Acyclic Nucleoside Phosphonates: A Key Class of Antiviral Drugs" Nat. Rev. Drug Discov. (2005) 4:928-940.
De Clerq et al., "Antiviral Agents Acting as DNA or RNA Chain Terminators" J. Handb. Exp. Pharmacol. (2009) 189:53-84.
Eriksson et al., "Synthesis and biological activation of an ethylene glycol-linked amino acid conjugate of cyclic cidofovir" Bioorg. Med. Chem. Lett. (2007) 17:583-586.
Eriksson et al., "Serine Peptide Phosphoester Prodrugs of Cyclic Cidofovir: Synthesis, Transport, and Antiviral Activity" Mol. Pharmaceutics (2008) 5(4):598-609.
Hakki et al., "The biology of cytomegalovirus drug resistance" Curr. Opin. Infect. Dis. (2011) 24:605-611.
Ruiz et al., "Synthesis and antiviral evaluation of alkoxyalkyl-phosphate conjugates of cidofovir and adefovir" Antiviral Research (2007) 75(1):87-90.
Otmar et al. "An Alternative Synthesis of HPMPC and HPMPA Diphosphoryl Derivatives" Coll. Czech. Chem. Comm. (2001) 66(3):500-506.
Topalis, et al., "Distribution and effects of amino acid changes in drug-resistant α and β herpesviruses DNA polymerase" Nucleic Acid Res. (2016) 44(20): 9530-9554.
Zakharova et al., "Tyrosine-Based 1-(S)-[3-Hydroxy-2-(phosphonomethoxy)propyl]cytosine and- adenine ((S)-HPMPC- and (S)-HPMPA) Prodrugs: Synthesis, Stability, Antiviral Activity, and in Vivo Transport Studies" J. Med. Chem. (2011) 54:5680-5693.
Zarrouk et al., "Herpesvirus DNA polymerases: Structures, functions and inhibitors" Virus Res. (2017) 234:177-192.

* cited by examiner

*Primary Examiner* — Joseph R Kosack
(74) *Attorney, Agent, or Firm* — Knobbe Martens Olson & Bear LLP

(57) ABSTRACT

The present invention relates to novel phosphonoamidate prodrugs. The invention also relates to the use of these novel phosphonate-modified nucleosides to treat or prevent viral infections and their use to manufacture a medicine to treat or prevent viral infections, particularly infections with viruses such as the herpes simplex virus 1, herpes simplex virus 2, human cytomegalovirus, varicella zoster virus, vaccinia virus and adenovirus.

12 Claims, No Drawings

PRODRUGS OF NUCLEOSIDE PHOSPHONATES

CROSS REFERENCE TO RELATED APPLICATIONS

This application is a U.S. National Phase Application of PCT International Application No. PCT/EP2018/057180, filed on Mar. 21, 2018, designating the United States of America and published in the English language, which claims priority to GB Application No. 1704577.4, filed Mar. 23, 2017 and GB 1711193.1, filed Jul. 12, 2017. The disclosures of the above-referenced applications are hereby expressly incorporated by reference in their entireties.

FIELD OF THE INVENTION

The present invention relates to novel phosphonoamidate prodrugs. The invention also relates to the use of these novel phosphonate-modified nucleosides to treat or prevent viral infections and their use to manufacture a medicine to treat or prevent viral infections, particularly infections with viruses such as the herpes simplex virus 1, herpes simplex virus 2, human cytomegalovirus, varicella zoster virus, vaccinia virus and adenovirus.

BACKGROUND OF THE INVENTION

Human herpesviruses are double-stranded DNA viruses belonging to the Herpesviridae family. This family includes nine human viruses, which are categorized in three subfamilies. The Alphaherpesvirinae is composed of the herpes simplex virus 1 and 2 (HSV-1 and HSV-2) and varicella-zoster virus (VZV). Human cytomegalovirus (HCMV) and human herpes viruses 6A, 6B and 7 (HHV-6A, HHV-6B and HH-7) belong to the Betaherpesvirinae subfamily. The third subfamily, the Gammaherpesvirinae, is composed of Epstein-Barr virus (EBV) and Kaposi's sarcoma associated herpes virus. Primary infection, as well as reactivation of herpesviruses, are responsible for a large spectrum of diseases. HSV-1 and HSV-2 cause orolabial and genital infections as well as keratitis and encephalitis. VZV is the causative agent of chickenpox and may reactivate to cause herpes zoster. HCMV is responsible for mononucleosis-like syndromes as well as systemic and organ-specific diseases (such as pneumonitis, hepatitis, retinitis, pancreatitis). HCMV infections in immunocompromised patients are severe and can be life-threatening. Infection with HHV-6B can give rise to roseola infantum, whereas primary infection with HHV-6A is generally asymptomatic. In immunocompromised patients, infections with HHV-6B and HHV-7 are also associated with severe diseases such as encephalitis and pneumonitis. The gamma-herpes viruses are oncogenic. EBV is associated with infectious mononucleosis, nasopharyngeal carcinoma, Burkitt's lymphoma and non-Hodgkin B-cell lymphoma. KSHV is mainly associated with Kaposi's sarcoma, one of the most frequently encountered neoplasms in HIV patients before the HAART era. All drugs currently marketed for the treatment of herpesvirus infections target the viral DNA polymerase [De Clercq *J. Antimicrob. Chemother.* 1993, 32 (Suppl. A), 121-132; De Clerq & Neyts, *J. Handb. Exp. Pharmacol.* 2009, 189, 53-84; Zarrouk et al. *Virus Res.* 2017, 234, 177-192]. These include acyclovir, ganciclovir, penciclovir and brivudine. For several of these compounds, the corresponding prodrug received also marketing approval, such as valacyclovir, valganciclovir and famciclovir. The antiviral activity of these "classical" nucleosides depends upon their intracellular metabolism within virus-infected cells to form sequentially the mono-, di-, and triphosphates. The triphosphates are the pharmacologically active species, as they are incorporated into the growing viral DNA strand by the viral DNA polymerases, resulting in chain termination or fraudulent DNA.

Cidofovir (background formula) is an acyclic nucleoside phosphonate (ANP) analogue, which is essentially a nucleoside monophosphate analogue, having the advantage of being metabolically stable. Because of the presence of a phosphonate moiety, cidofovir is independent of viral kinases for activation and they only need two phosphorylation steps which are carried out by cellular kinases [De Clercq Clin. *Microb. Rev.* 2003, 16, 569-596]. Besides its activity against herpesviruses, Cidofovir is endowed with broad-spectrum activity against virtually all DNA viruses, including adeno-, polyoma-, papilloma- and poxviruses. Among the poxviruses, vaccinia, variola (smallpox), cowpox, monkeypox, camelpox, molluscum contagiosum and orf have proven sensitive to the inhibitory effects of cidofovir. In vivo, cidofovir has shown high efficacy, even after administration of a single systemic (intraperitoneal) or intranasal (aerosolized) dose, in protecting mice from a lethal respiratory infection with either vaccinia or cowpox. Cidofovir has also demonstrated high effectiveness in the treatment of vaccinia virus infection in severe combined immune deficiency mice [De Clercq *Antiviral Research* 2002, 55, 2002, 1-13]. Foscarnet is a pyrophosphate analogue that directly interacts with the DNA polymerase and therefore is independent of activation by viral kinases.

The emergence of drug-resistant herpesvirus strains has been increasing in the past decade [Hakki & Chou *Curr. Opin. Infect. Dis.* 2011, 24, 605-611; Campos et al. *Rev. Med. Virol.* 2016, 26, 161-182; Topalis, et al. *Nucleic Acid Res.* 2016, 44, 9530-9554]. Long-term exposure to these antiviral drugs and/or suboptimal doses selects for mutations leading to drug-resistance. Well-known mutations linked to drug resistance are either in the viral kinase or in the viral DNA polymerase. Mutations in the gene encoding for the kinase do not affect susceptibility to cidofovir and foscarnet. As a result, foscarnet is only used as second-line treatment of drug-resistant herpesvirus strains resistant to acyclovir (HSV and VZV) or ganciclovir (HCMV) with mutations in viral kinases. Cidofovir is being used only for multi-drug resistant strains with decreased sensitivity to nucleoside analogues and foscarnet. In recent years, resistance to cidofovir and foscarnet is emerging (due to mutations in the DNA polymerase gene), especially in immunocompromised patients (HIV and transplant patients), further reducing the number of therapeutic options.

Besides the emergence of cidofovir-resistant herpesviruses, cidofovir has also other shortcomings. Cidofovir, being an ANP analogue, is metabolically stable. However, the phosphonate moiety is negatively charged at physiological pH, and hence, cidofovir is not able to penetrate the lipid-rich cell membrane, which hampers its antiviral activity, as well as its oral bioavailability [De Clercq *Antiviral Research* 2002, 55, 2002, 1-13]. Moreover, cidofovir causes renal insufficiency, due to the fact that it is actively transported into renal proximal tubular cells more rapidly than it is secreted and accumulates to toxic levels [De Clercq & Holy *Nat. Rev. Drug Discov.* 2005, 4, 928-940]. Therefore, the development of an orally bioavailable, less toxic prodrug form of cidofovir is highly desirable.

In order to decrease the nephrotoxicity of cidofovir, cyclic cidofovir (cHPMPC, background formula) has been synthesized [Bischofberger et al. *Antimicrob. Agents Chemother.* 1994, 38, 2387-2391]. It has been shown to have a similar antiviral activity as HPMPC against CMV and HSV when tested in vitro assays. Also cHPMPC and HPMPC have similar potencies in vivo, as shown in a mouse HSV-2 encephalitis model. Unfortunately, cHPMPC still suffers from a low oral bioavailability, due to the residual phosphonate negative charge at physiological pH.

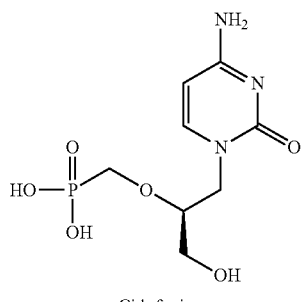

Cidofovir

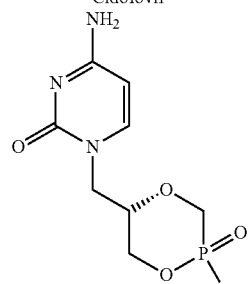

Cyclic cidofovir
(cHPMPC)

Formulas Background

Different prodrug strategies have been developed in order to mask this negative charge. All current prodrug approaches for cHPMPC are phosphoester prodrugs. Examples include ether-lipid conjugates, ethylene-glycol-linked amino acids conjugates, and serine dipeptide phosphoester prodrugs [Eriksson et al. *Mol. Pharmaceutics* 2008, 5, 598-609; Eriksson et al. *Bioorg. Med. Chem. Lett.* 2007, 17, 583-586; Zakharova *J. Med. Chem.* 2011, 54, 5680-5693]. On the other hand, phosphonoamidate prodrugs of cHPMPC have been hardly explored. The only exception being phosphonoamidate prodrugs using L-alanine ester groups as amino acid motif. These were evaluated for their ability to inhibit the replication of vaccinia virus or cowpox virus in tissue culture cells, but were found to be only marginally active, with $EC_{50}$ values in the range of 4-27 μM [Keith, K. A. et al. *Antimicrob. Agents Chemother.* 2003, 47, 2193-2198].

The present invention is based on the unexpected finding that phosphonoamidate prodrugs of ANPs with a (1-[-2-hydroxy-2-oxido-1,4,2-dioxaphosphorinan-5-yl] methyl side chain show unexpected biological properties, in particular have significant antiviral activity against the herpes simplex virus 1, the herpes simplex virus 2, the human cytomegalovirus, the varicella zoster virus, the vaccinia virus and the adenovirus.

SUMMARY OF THE INVENTION

The present invention relates to novel phosphonoamidate prodrugs of ANPs with a 3-hydroxy-2-(phosphonomethoxy)-propyl (HPMP) or it cyclized counterpart (1-[-2-hydroxy-2-oxido-1,4,2-dioxaphosphorinan-5-yl]methyl] side chain and their use as agents for treating viral diseases. It is based on the unexpected finding that certain of these nucleotide prodrugs show unexpected biological properties, in particular have significant activity against the herpes simplex virus 1, the herpes simplex virus 2, the human cytomegalovirus, the varicella zoster virus, the vaccinia virus and the adenovirus.

Numbered statements of the invention are:
1. A compound of formula Ia:

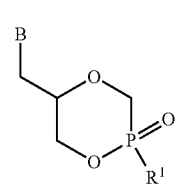

wherein
B is a natural or modified nucleobase;
$R^1$ has the general formula II

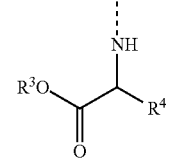

wherein
$R^3$ is selected from the group consisting of aryl, heteroaryl, $C_1$-$C_{10}$ alkyl, $C_3$-$C_8$-cycloalkyl, $C_3$-$C_8$-cycloalkyl-alkyl, aryl($C_1$-$C_6$)alkyl, $C_2$-$C_{10}$ alkenyl, $C_2$-$C_{10}$ alkynyl, hydroxyl $C_1$-$C_{10}$ alkyl, halo $C_1$-$C_{10}$ alkyl, and alkoxyalkyl;
$R^4$ is selected from the group consisting of aryl, heteroaryl, $C_1$-$C_{10}$ alkyl, $C_3$-$C_8$-cycloalkyl, $C_3$-$C_8$-cycloalkyl-alkyl, aryl($C_1$-$C_6$)alkyl, $C_2$-$C_{10}$ alkenyl, $C_2$-$C_{10}$ alkynyl, hydroxyl $C_1$-$C_{10}$ alkyl, halo $C_1$-$C_{10}$ alkyl, alkoxyalkyl, X—$COOR^5$, X—O(C=O)—$R^5$;
wherein X is aryl, heteroaryl, $C_1$-$C_{10}$ alkyl, $C_2$-$C_{10}$ alkenyl, $C_2$-$C_{10}$ alkynyl, or $C_3$-$C_8$-cycloalkyl, and wherein said aryl, heteroaryl, $C_1$-$C_{10}$ alkyl, $C_2$-$C_{10}$ alkenyl, $C_2$-$C_{10}$ alkynyl, $C_3$-$C_8$-cycloalkyl optionally contains one or more functions, atoms or radicals independently selected from the group consisting of halogen, halo-alkyl, cyano, $C_1$-$C_7$ alkoxy; and
wherein $R^5$ is selected from the group consisting of aryl, heteroaryl, $C_1$-$C_{10}$ alkyl, $C_3$-$C_8$-cycloalkyl, $C_3$-$C_8$-cycloalkyl-alkyl, aryl($C_1$-$C_6$)alkyl, $C_2$-$C_{10}$ alkenyl, $C_2$-$C_{10}$ alkynyl, hydroxyl $C_1$-$C_{10}$ alkyl, halo $C_1$-$C_{10}$ alkyl, and alkoxyalkyl;
and/or a pharmaceutical acceptable addition salt thereof and/or a stereoisomer thereof and/or a solvate thereof; and
wherein said compound is not:
(Ethyl-L-alaninyl) cyclic HPMPC;
(Phenylethyl-L-alaninyl) cyclic HPMPC; or
(Butyl-L-alaninyl) cyclic HPMPC.
2. The compound according to statement 1, wherein B is selected from the group of adenine, thymine, cytosine and guanine.

3. The compound according to statement 1 or 2, wherein $R^3$ is selected from $C_1$-$C_{10}$ alkyl.

4. The compound according to any one of statements 1 to 3, wherein $R^4$ is X—COOR$^5$ and wherein X is aryl, heteroaryl, $C_1$-$C_{10}$ alkyl, $C_2$-$C_{10}$ alkenyl, $C_2$-$C_{10}$ alkynyl, or $C_3$-$C_8$-cycloalkyl, and wherein said aryl, heteroaryl, $C_1$-$C_{10}$ alkyl, $C_2$-$C_{10}$ alkenyl, $C_2$-$C_{10}$ alkynyl, $C_3$-$C_8$-cycloalkyl optionally contains one or more functions, atoms or radicals independently selected from the group consisting of halogen, halo-alkyl, cyano, $C_1$-$C_7$ alkoxy; and wherein $R^5$ is selected from the group consisting of aryl, heteroaryl, $C_1$-$C_{10}$ alkyl, $C_3$-$C_8$-cycloalkyl, $C_3$-$C_8$-cycloalkyl-alkyl, aryl($C_1$-$C_6$)alkyl, $C_2$-$C_{10}$ alkenyl, $C_2$-$C_{10}$ alkynyl, hydroxyl $C_1$-$C_{10}$ alkyl, halo $C_1$-$C_{10}$ alkyl, and alkoxyalkyl.

5. The compound according to any one of statements 1 to 4, wherein X is $C_1$-$C_{10}$ alkyl and $R^5$ is $C_1$-$C_{10}$ alkyl.

6. The compound according to statement 1, selected from the group consisting of Diamyl {(5S)-5-[(6-amino-9H-purin-9-yl)methyl]-2-oxido-1,4,2-dioxaphosphinan-2-yl}-L-aspartate; Diamyl {(5R)-5-[(6-amino-9H-purin-9-yl)methyl]-2-oxido-1,4,2-dioxaphosphinan-2-yl}-L-aspartate; Diamyl {(5S)-5-[(4-amino-2-oxopyrimidin-1(2H)-yl)methyl]-2-oxido-1,4,2-dioxaphosphinan-2-yl}-L-aspartate; diamyl {(5R)-5-[(4-amino-2-oxopyrimidin-1(2H)-yl)methyl]-2-oxido-1,4,2-dioxaphosphinan-2-yl}-L-aspartate; Amyl ((5S)-5-((6-amino-9H-purin-9-yl)methyl)-2-oxido-1,4,2-dioxaphosphinan-2-yl)-L-phenylalaninate; Amyl ((5S)-5-((6-amino-9H-purin-9-yl)methyl)-2-oxido-1,4,2-dioxaphosphinan-2-yl)-L-methioninate; Amyl ((5S)-5-((6-amino-9H-purin-9-yl)methyl)-2-oxido-1,4,2-dioxaphosphinan-2-yl)-L-alaninate; Diamyl {(5S)-5-[(6-amino-9H-purin-9-yl)methyl]-2-oxido-1,4,2-dioxaphosphinan-2-yl}-L-glutamate; Amyl {(5S)-5-[(6-amino-9H-purin-9-yl)methyl]-2-oxido-1,4,2-dioxaphosphinan-2-yl}-L-valinate; Amyl {(5S)-5-[(6-amino-9H-purin-9-yl)methyl]-2-oxido-1,4,2-dioxaphosphinan-2-yl}-L-leucinate; Amyl {(5S)-5-[(6-amino-9H-purin-9-yl)methyl]-2-oxido-1,4,2-dioxaphosphinan-2-yl}-L-isoleucinate; diamyl 2,2'-((((((S)-1-(6-amino-9H-purin-9-yl)-3-hydroxypropan-2-yl)oxy)methyl)phosphoryl)bis(azanediyl))(2S,2'S)-bis(3-methylbutanoate); amyl {(5S)-5-[(4-amino-2-oxopyrimidin-1(2H)-yl)methyl]-2-oxido-1,4,2-dioxaphosphinan-2-yl}-L-phenylalaninate; diamyl ((5S)-5-((4-amino-2-oxopyrimidin-1(2H)-yl)methyl)-2-oxido-1,4,2-dioxaphosphinan-2-yl)-L-glutamate; amyl ((5S)-5-((4-amino-2-oxopyrimidin-1(2H)-yl)methyl)-2-oxido-1,4,2-dioxaphosphinan-2-yl)-L-valinate; amyl ((5S)-5-((4-amino-2-oxopyrimidin-1(2H)-yl)methyl)-2-oxido-1,4,2-dioxaphosphinan-2-yl)-L-leucinate amyl ((5S)-5-((4-amino-2-oxopyrimidin-1(2H)-yl)methyl)-2-oxido-1,4,2-dioxaphosphinan-2-yl)-L-isoleucinate; and diamyl ((5S)-5-((4-amino-2-oxopyrimidin-1(2H)-yl)methyl)-2-oxido-1,4,2-dioxaphosphinan-2-yl)-D-aspartate.

7. A compound according to any one of statements 1 to 6 for use as a medicine.

8. A compound according to any one of statements 1 to 6 for use in the prevention or treatment of a viral infection in an animal, mammal or human.

9. The compound for use according to statement 8, wherein said viral infection is an infection selected from the group consisting of the hepatitis B virus (HBV), the human immunodeficiency virus (HIV), varicella-zoster virus (VZV), cytomegalovirus (CMV), vaccinia virus (VV), herpes simplex virus (HSV), BK virus, Epstein-barr virus (EBV), papillomavirus, Monkeypox virus, Cowpox virus, hepatitis C virus (HCV), respiratory syncytial virus (RSV), dengue virus, influenza virus, adenovirus, parainfluenza virus and/or rhinovirus.

10. A compound according to any one of statements 1 to 6 for use as in the prevention or treatment of a proliferative disorder such as cancer in an animal, mammal or human.

11. A pharmaceutical composition comprising a therapeutically effective amount of a compound according to any one of statements 1 to 6 and one or more pharmaceutically acceptable excipients.

12. The pharmaceutical composition according to statement 11, further comprising one or more biologically active drugs being selected from the group consisting of antiviral drugs and/or anti-proliferative drugs.

13. A method of prevention or treatment of a viral infection in an animal, mammal or human, comprising the administration of a therapeutically effective amount of a compound according to any one of statements 1 to 6, optionally in combination with one or more pharmaceutically acceptable excipients.

14. A method of prevention or treatment of a proliferative disorder in an animal, mammal or human, comprising the administration of a therapeutically effective amount of a compound according to any one of statements 1 to 6, optionally in combination with one or more pharmaceutically acceptable excipients.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION OF THE INVENTION

Scheme 1 schematically shows a method for the preparation of phosphonoamidate prodrugs of cHPMPA (compounds 4a/b) and cHPMPC (compounds 5a/b). The starting materials 1a/b and 2a/b are accessible according to literature procedures (*Antiviral Research* 2007, 75, 87-90; *Coll. Czech. Chem. Comm.* 2001, 66, 500-506).

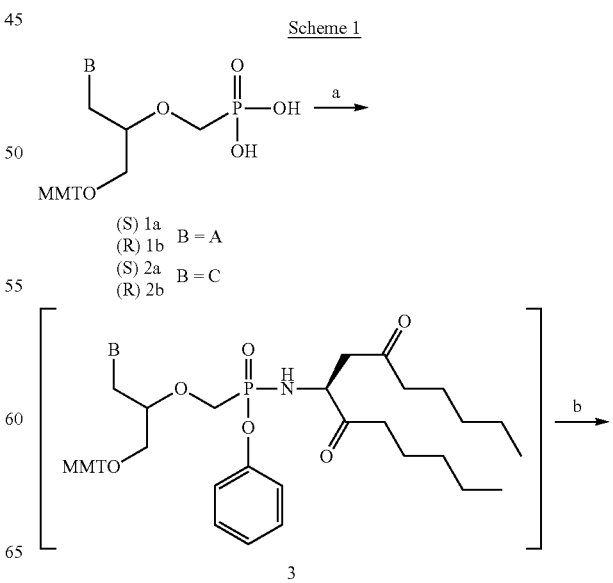

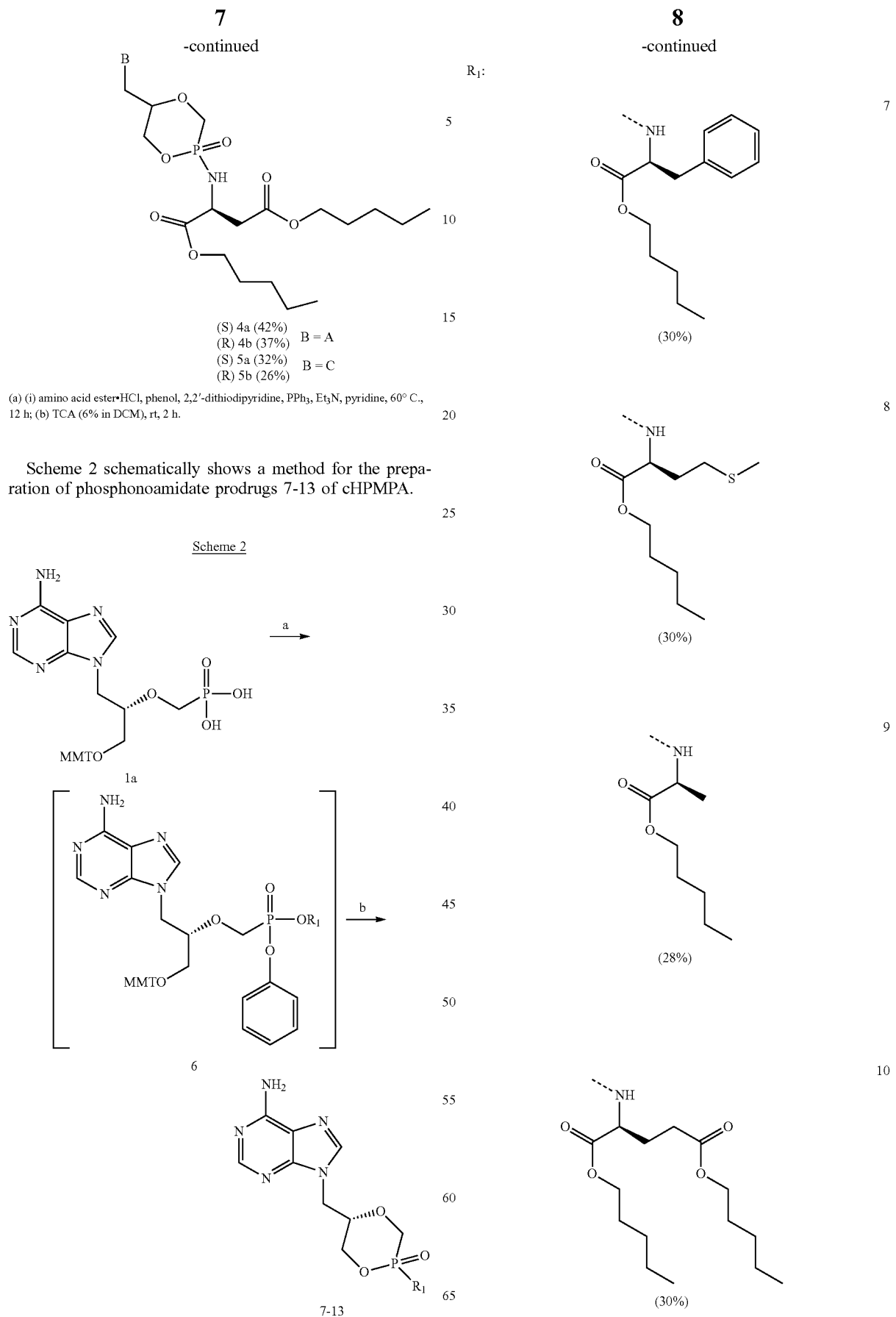
(a) (i) amino acid ester·HCl, phenol, 2,2′-dithiodipyridine, PPh₃, Et₃N, pyridine, 60° C., 12 h; (b) TCA (6% in DCM), rt, 2 h.
Scheme 2 schematically shows a method for the preparation of phosphonoamidate prodrugs 7-13 of cHPMPA.

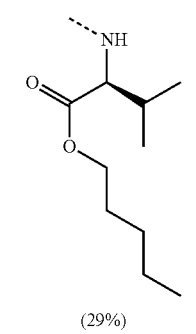

(29%)

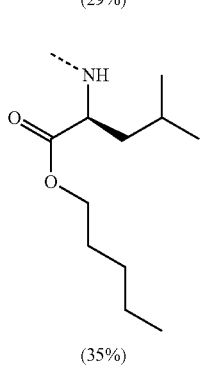

(35%)

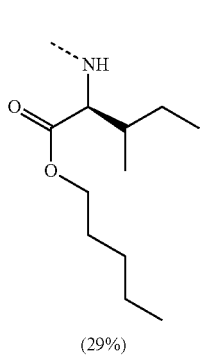

(29%)

(a) Amino acid ester•HCl, phenol, 2,2′-dithiodipyridine, PPh₃, Et₃N, pyridine, 60° C., 12 h; (b) TCA (6% in DCM), rt, 2 h.

Scheme 3 schematically shows the synthesis of a phosphonobisamidate prodrug of cHPMPA.

Scheme 3

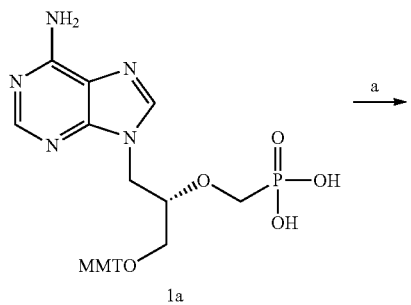

1a

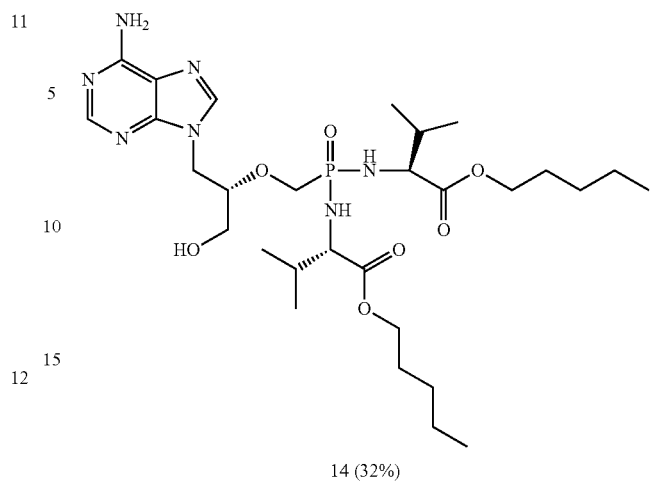

14 (32%)

(a) (i) amino acid ester•HCl, 2,2′-dithiodipyridine, PPh₃, Et₃N, pyridine, 60° C., 12 h; (ii) TCA (6% in DCM), rt, 2 h.

Scheme 4 schematically shows a method for the preparation of a series of phosphonoamidate prodrugs of cHPMPC.

Scheme 4

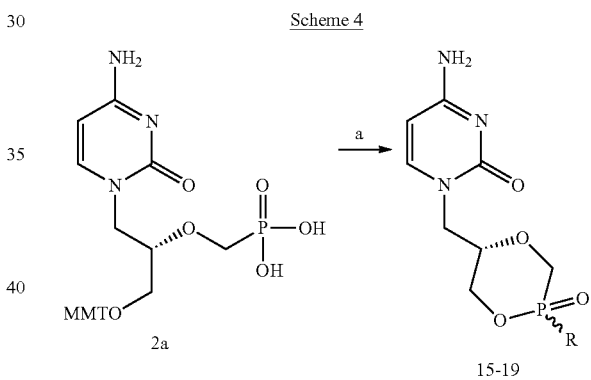

2a    15-19

R:

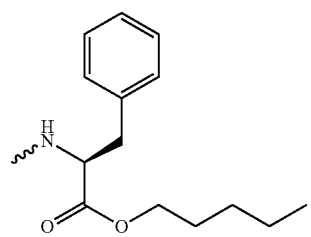

15

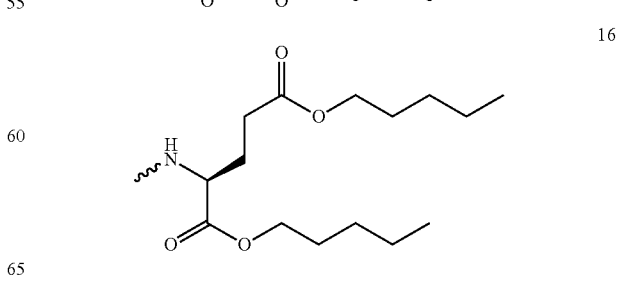

16

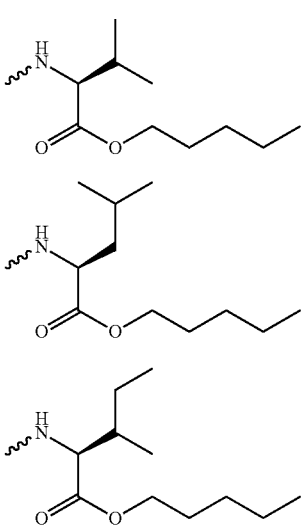

17

18

19

(a) (i) amino acid ester•HCl, phenol, 2,2′-dithiodipyridine, PPh$_3$, Et$_3$N, pyridine, 60° C., 12 h; (ii) TCA (6% in DCM), rt, 2 h.

According to one embodiment, the present invention encompasses compounds of the general formula Ia and Ib:

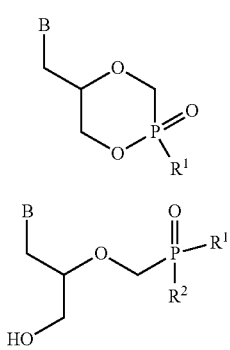

Ia

Ib wherein
B is any natural or modified nucleobase
R$^1$ and R$^2$ have the general formula II

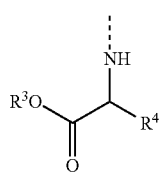

II wherein
R$^3$ is selected from the group consisting of aryl, heteroaryl, C$_1$-C$_{10}$ alkyl, C$_3$-C$_8$-cycloalkyl, C$_3$-C$_8$-cycloalkyl-alkyl, aryl(C$_1$-C$_6$)alkyl, C$_2$-C$_{10}$ alkenyl, C$_2$-C$_{10}$ alkynyl, hydroxyl C$_1$-C$_{10}$ alkyl, halo C$_1$-C$_{10}$ alkyl, and alkoxyalkyl;
R$^4$ is selected from the group consisting of aryl, heteroaryl, C$_1$-C$_{10}$ alkyl, C$_3$-C$_8$-cycloalkyl, C$_3$-C$_8$-cycloalkyl-alkyl, aryl(C$_1$-C$_6$)alkyl, C$_2$-C$_{10}$ alkenyl, C$_2$-C$_{10}$ alkynyl, hydroxyl C$_1$-C$_{10}$ alkyl, halo C$_1$-C$_{10}$ alkyl, alkoxyalkyl, X—COOR$^5$, X—O(C=O)—R$^5$;

wherein X is aryl, heteroaryl, C$_1$-C$_{10}$ alkyl, C$_2$-C$_{10}$ alkenyl, C$_2$-C$_{10}$ alkynyl, or C$_3$-C$_8$-cycloalkyl, and wherein said aryl, heteroaryl, C$_1$-C$_{10}$ alkyl, C$_2$-C$_{10}$ alkenyl, C$_2$-C$_{10}$ alkynyl, C$_3$-C$_8$-cycloalkyl optionally contains one or more functions, atoms or radicals independently selected from the group consisting of halogen, halo-alkyl, cyano, C$_1$-C$_7$ alkoxy; and
wherein R$^5$ is selected from the group consisting of aryl, heteroaryl, C$_1$-C$_{10}$ alkyl, C$_3$-C$_8$-cycloalkyl, C$_3$-C$_8$-cycloalkyl-alkyl, aryl(C$_1$-C$_6$)alkyl, C$_2$-C$_{10}$ alkenyl, C$_2$-C$_{10}$ alkynyl, hydroxyl C$_1$-C$_{10}$ alkyl, halo C$_1$-C$_{10}$ alkyl, and alkoxyalkyl;
R$^1$ and R$^2$ are different or identical;
and/or a pharmaceutical acceptable addition salt thereof and/or a stereoisomer thereof and/or a solvate thereof; and
wherein said compound is not:
(Ethyl-L-alaninyl) cyclic HPMPC;
(Phenylethyl-L-alaninyl) cyclic HPMPC; or
(Butyl-L-alaninyl) cyclic HPMPC.

Said base (B) is selected from the group of the pyrimidine and purine bases. Such bases include natural bases, such as adenine, thymine, cytosine, uracyl, guanine and modified bases or modifications or analogues of said natural bases. In certain embodiments of the present invention said base is a guanine, cytosine, adenine, thymine, cytosine, or uracyl. In a more specific embodiment of the present invention, said base is a adenine or guanine. In another specific embodiment of the present invention said base is a cytosine. In another specific embodiment of the present invention said base is a thymine. In another specific embodiment of the present invention said base is uracil.

In another embodiment, the present invention concerns a compound according to the invention, including the compound of formula Ib, or any subgroup thereof, wherein R$^1$ and R$^2$ have the general formula II and R$^1$ and R$^2$ are identical. In another embodiment, the present invention concerns a compound according to the invention, including the compound of formula Ib, or any subgroup thereof, wherein R$^1$ and R$^2$ are different and both R$^1$ and R$^2$ are of the general formula II.

In a more specific embodiment said R$^3$ is C$_1$-C$_{10}$ alkyl. In another specific embodiment said R$^3$ is C$_3$-C$_{10}$ alkyl. In another specific embodiment said R$^3$ is C$_1$-C$_5$ alkyl. In yet another specific embodiment said R$^3$ is C$_3$-C$_5$ alkyl. In yet another specific embodiment said R$^3$ is C$_5$ alkyl.

In another specific embodiment, the present invention concerns a compound according to the invention, including the compound of formula Ia, wherein R$^3$ is selected from the group consisting of aryl, heteroaryl, C$_3$-C$_{10}$ alkyl, C$_3$-C$_8$-cycloalkyl, C$_3$-C$_8$-cycloalkyl-alkyl, C$_2$-C$_{10}$ alkenyl, C$_2$-C$_{10}$ alkynyl, hydroxyl C$_1$-C$_{10}$ alkyl, halo C$_1$-C$_{10}$ alkyl, and alkoxyalkyl.

In another specific embodiment said R$^3$ is not substituted or unsubstituted ethyl.

In another specific embodiment, the present invention concerns a compound according to the invention, including the compound of formula Ia, wherein R$^1$ is not an alaninyl group. In a more specific embodiment thereof, said R$^1$ is not an alkyl- or phenyl-substituted alaninyl group.

In another specific embodiment, said R$^4$ is selected from the group consisting of C$_1$-C$_{10}$ alkyl or X—COOR$^5$, wherein R$^5$ can have any values as described herein. In a more specific embodiment, said R$^5$ is selected from the group consisting of aryl, heteroaryl, C$_1$-C$_{10}$ alkyl, C$_3$-C$_8$-cycloalkyl, C$_3$-C$_8$-cycloalkyl-alkyl, aryl(C$_1$-C$_6$)alkyl, C$_2$-C$_{10}$ alkenyl, C$_2$-C$_{10}$ alkynyl, hydroxyl C$_1$-C$_{10}$ alkyl, halo C$_1$-C$_{10}$ alkyl, and alkoxyalkyl. In a more specific embodiment R$^5$ is C$_1$-C$_7$ alkyl or C$_3$-C$_8$ cycloalkyl; in a more specific embodiment $R^5$ is $C_1$-$C_5$ alkyl, and in another more specific embodiment $R^5$ is $C_3$-$C_7$ alkyl, in an even more specific embodiment $R^5$ is $C_3$-$C_5$ alkyl. In a yet more specific embodiment $R^5$ is $C_5$ alkyl. In another specific embodiment, $R^5$ is aryl-($C_1$-$C_2$)alkyl; in another more specific embodiment, $R^5$ is benzyl or phenyl-methyl.

In another specific embodiment, X is selected from the group consisting of aryl, heteroaryl, $C_1$-$C_{10}$ alkyl, $C_2$-$C_{10}$ alkenyl, $C_2$-$C_{10}$ alkynyl or $C_3$-$C_8$-cycloalkyl, and wherein said aryl, heteroaryl, $C_1$-$C_{10}$ alkyl, and $C_3$-$C_8$-cycloalkyl optionally contains one or more functions, atoms or radicals independently selected from the group consisting of halogen, carbonyl, thiocarbonyl, hydroxyl, thiol, ether, thio-ether, acetal, thio-acetal, amino, imino, oximino, alkyloximino, aminoacid, cyano, acylamino, thioacylamino, carbamoyl, thiocarbamoyl, ureido, thio-ureido, carboxylic acid ester or halide or anhydride or amide, thiocarboxylic acid or ester or thioester or halide or anhydride or amide, nitro, thio $C_{1-7}$ alkyl, thio $C_3$-$C_{10}$ cycloalkyl, hydroxylamino, mercaptoamino, alkyl-amino, cycloalkylamino, alkenylamino, cycloalkenylamino, alkynylamino, arylamino, arylalkylamino, hydroxyalkylamino, mercaptoalkylamino, heterocyclic-substituted alkylamino, hetero-cyclic amino, heterocyclic-substituted arylamino, hydrazine, alkylhydrazino, phenylhydrazino, sulfonyl, sulfinyl and sulfonamide. In a more specific embodiment, X is selected from the group consisting of aryl, heteroaryl, $C_1$-$C_{10}$ alkyl, or $C_3$-$C_8$-cycloalkyl, more specifically said X is a $C_1$-$C_6$ alkyl, even more specifically said X is a $C_1$-$C_3$ alkyl or $C_1$-$C_2$ alkyl or —$CH_2$—.

Special novel compounds in accordance with the present invention include each of the compounds whose preparation is described in the accompanying Examples, and pharmaceutically acceptable salts and solvates thereof.

The present invention also concerns a compound having formula Ia, Ib, or any subgroup thereof, or stereoisomeric forms thereof, for use as a medicine.

The present invention also concerns a compound having formula Ia, Ib, or any subgroup thereof, or stereoisomeric forms thereof, for use as a medicine for the prevention or treatment of viral disorders and oncological disorders in an animal, preferably in a mammal. In an embodiment, said disorder is a viral disorder, including a disease caused by a viral infection, for example an infection with HBV, HIV, HCV, RSV, dengue virus, influenza virus, VZV, CMV, adenovirus, vaccinia virus, parainfluenza, rhinovirus, BK virus, and/or HSV; in another embodiment said disorder is an oncological disorder, which may be acute or chronic, including a proliferative disorder, especially cancer. In an embodiment, said mammal is a human being. In a specific embodiment, said compounds for use as a medicine, in particular for the prevention or treatment of viral disorders, are the compounds of formula Ia and Ib, including any subgroups thereof. In a more specific embodiment thereof, said compounds of formula Ia and Ib have as a base B a pyrimidine base, more specifically a pyrimidine base represented by the structural formula (IV):

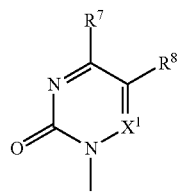

IV or
a purine base, more specifically a purine base represented by the structural formula (V):

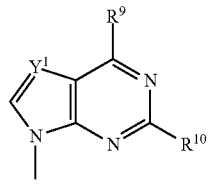

V wherein:
$R^7$ and $R^9$ are independently selected from the group consisting of H, —OH, —SH, —$NH_2$, and —NH-Me;
$R^8$ and $R^{10}$ are independently selected from the group consisting of H, methyl, ethyl, isopropyl, hydroxyl, amino, ethylamino, trifluoromethyl, cyano and halogen; and
$X^1$ and $Y^1$ are independently selected from CH and N.

The present invention also concerns the use of the compounds of formula Ia, Ib, or any subgroup thereof, or stereoisomeric forms thereof, for the manufacture of a medicament for the prevention or treatment of a viral disorder and/or an oncological disorder in an animal. In an embodiment, said animal is a mammal, preferably said mammal is a human being.

In a further specific embodiment, said viral disorder is a disease caused by a viral infection, for example an infection with HBV, HIV, HCV, RSV, dengue virus, influenza virus, CMV, VZV, adenovirus, vaccinia virus, parainfluenza, rhinovirus, BK virus, and/or HSV. In an even more specific embodiment said viral disorder is a disease caused by a viral infection with HSV, CMV and/or VZV. In a specific embodiment, said viral disorder is a disease caused by a viral infection with CMV.

The present invention also concerns a pharmaceutical composition comprising a therapeutically effective amount of a compound having formula Ia, Ib, or any subgroup thereof, or stereoisomeric forms thereof and one or more pharmaceutically acceptable excipients. Said composition may further comprise one or more biologically active drugs being selected from the group consisting of antiviral drugs, and antineoplastic drugs.

The present invention also concerns a method of prevention or treatment of a viral disorder in an animal, comprising the administration of a therapeutically effective amount of a compound having formula Ia, Ib, or any subgroup thereof, or stereoisomeric forms thereof, optionally in combination with one or more pharmaceutically acceptable excipients.

The present invention also concerns a method of prevention or treatment of an oncological disorder in an animal, comprising the administration of a therapeutically effective amount of a compound having formula Ia, Ib, or any subgroup thereof, or stereoisomeric forms thereof, optionally in combination with one or more pharmaceutically acceptable excipients.

For use in medicine, the salts of the compounds of formula Ia or Ib, will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula Ia and Ib above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula Ia and Ib may be formed with water, in which case they will be hydrates.

The compounds in accordance with the present invention are beneficial in the treatment and/or prevention of various animal, mammal or human ailments or diseases. These include viral diseases, such as diseases caused by a viral infection, for example an infection with HBV, HIV, HCV, RSV, dengue virus, influenza virus, herpes simplex viruses 1 and 2 (HSV-1 and HSV-2), varicella-zoster virus (VZV), Epstein-Barr virus (EBV or HHV-4), human cytomegalovirus (HCMV or HHV-5), human herpesvirus 6A and 6B (HHV-6A and HHV-6B), human herpesvirus 7 (HHV-7), and Kaposi's sarcoma-associated herpesvirus (KSHV, also known as HHV-8), adenovirus, vaccinia virus, parainfluenza, rhinovirus, and/or BK virus; and oncological disorders such as proliferative disorders (eg. cancer).

Viral diseases include infections caused by various families of virus, including the Hepadnaviridae, Retroviridae, Herpesviridae, Papovaviridae, Papillomaviridae or pappilomaviruses, Flaviviridae, Picornaviridae. Various genera within the Hepadnaviridae include the genera Orthohepadnavirus and the Avihepadnavirus; Members of the Orthohepadnavirus genus include hepatitis B virus (HBV) and the Woodchuck hepatitis virus. Members of the Avihepadnavirus genus include the Duck hepatitis B virus. Various genera within the Retroviridae family include Alpharetrovirus, Betaretrovirus, Gammaretrovirus, Deltaretrovirus, Epsilonretrovirus, Lentivirus and Spumavirus. Members of the Lentivirus genus include human immunodeficiency virus 1 (HIV-1) and human immunodeficiency virus 2 (HIV-2). Various genera within the Herpesviridae family include (i) within the subfamily of the Alphaherpesvirinae: Varicellovirus, Scutavirus, Iltovirus, Mardivirus, Simplexvirus; (ii) within the subfamily of the Betaherpesvirinae: Cytomegalovirus, Muromegalovirus, Proboscivirus, Roseolovirus; and (iii) within the subfamily of the Gammaherpesvirinae: Lymphocryptovirus, Macavirus, Percavirus, Rhadinovirus. Members of the Varicellovirus genus include Varicella zoster virus (VZV); Simian varicella virus; Phocine herpesvirus 1; Suid herpesvirus 1; Feline herpesvirus 1; Equine herpesvirus 1, 3, 4, 8 and 9; Cervine herpesvirus 1, and 2; Cercopithecine herpesvirus 9; Caprine herpesvirus 1; Bovine herpesvirus 1 and 5; Bubaline herpesvirus 1; Canine herpesvirus 1. Members of the Simplexvirus genus include Human herpesvirus 1 and 2. Members of the Scutavirus genus include Chelonid herpesvirus 5. Members of the Iltovirus genus include Gallid herpesvirus 1. Members of the Mardivirus genus include Gallid herpesvirus 2. Members of the Cytomegalovirus genus include Human cytomegalovirus (CMV). Members of the Proboscivirus genus include Elephantid herpesvirus 1. Members of the Muromegalovirus genus include Murid herpesvirus 1. Members of the Roseolovirus genus include Human herpesvirus 6A, 6B and 7. Members of the Lymphocryptovirus genus include Human herpesvirus 4. Members of the Macavirus genus include Alcelaphine herpesvirus 1. Members of the Percavirus genus include Equid herpesvirus 2. Members of the Rhadinovirus genus include Saimiriine herpesvirus 2, Kaposi's sarcoma-associated virus. Various genera within the Flaviviridae family include Flavivirus, Pestivirus, Hepacivirus and Hepatitis G Virus. The Papovaviridae family include the genus Polyomavirus (e.g. JC virus; BK virus; Merkel cell polyomavirus; Trichodysplasia spinulosa polyomavirus; Human polyomavirus 6, 7, 9 and 12; New Jersey polyomavirus; KI polyomavirus; WU polyomavirus; MW polyomavirus; STL polyomavirus). The Pappilomaviridae or pappilomaviruses include the human pappilomaviruses (HPV). Members of the Flavivirus genus include Dengue fever virus, yellow fever virus, West Nile encephalitis virus and Japanese encephalitis virus. Members of the Pestivirus genus include bovine viral diarrhoea virus (BVDV), classical swine fever virus and border disease virus 2 (BDV-2). Members of the Hepacivirus genus include hepatitis C virus (HCV). Members of the Hepatitis G Virus genus include hepatitis G virus. Various genera within the Picornaviridae family include Aphthovirus, Avihepatovirus, Cardiovirus, Enterovirus, Erbovirus, Hepatovirus, Kobuvirus, Parechovirus, Sapelovirus, Senecavirus, Teschovirus and Tremovirus. Members of the Enterovirus genus include poliovirus, coxsackie A virus, coxsackie B virus and rhinovirus.

Oncological disorders, which may be acute or chronic, include proliferative disorders, especially cancer, in animals, including mammals, especially humans. Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle.

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

The quantity of a compound of use in the invention required for the prophylaxis or treatment of a particular condition or disease will vary depending on the compound chosen and the condition of the animal, mammal or human patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

DEFINITIONS

The term "natural or modified nucleobase" refers to any base B of the "pyrimidine and purine bases" as used herein and includes, but is not limited to, adenine, thymine, cytosine, uracyl, guanine, 2,6-diaminopurine, 5-fluorocytosine, 5-fluorouracil, 7-deazaguanosine, 7-deazaadenine and modifications or analogues thereof. A purine or pyrimidine base as used herein includes a purine or pyrimidine base found in naturally occurring nucleosides as mentioned above. An analogue thereof is a base which mimics such naturally occurring bases in such a way that their structures (the kinds of atoms and their arrangement) are similar to the naturally occurring bases but may either possess additional or lack certain of the functional properties of the naturally occurring bases. Such analogues include those derived by replacement of a CH moiety by a nitrogen atom (e.g. 5-azapyrimidines such as 5-azacytosine) or vice versa (e.g. 7-deazapurines, such as 7-deazaadenine or 7-deazaguanine) or both (e.g., 7-deaza, 8-azapurines). Analogues include those bases wherein ring substituents are either incorporated, removed, or modified by conventional substituents known in the art, e.g. halogen, hydroxyl, amino, ($C_1$-$C_6$) alkyl and others. Such purine or pyrimidine bases, and analogues thereof, are well known to those skilled in the art, e.g. as shown at pages 20-38 of WO 03/093290.

In particular purine and pyrimidine analogues B for the purpose of the present invention may be selected from the group comprising pyrimidine bases represented by the structural formula (IV):

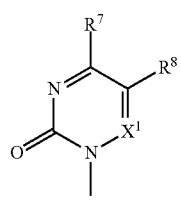

IV and purine bases represented by the structural formula (V):

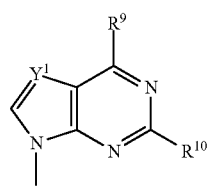

V wherein:

$R^7$ and $R^9$ are independently selected from the group consisting of H, —OH, —SH, —$NH_2$, and —NH-Me;

$R^8$ and $R^{10}$ are independently selected from the group consisting of H, methyl, ethyl, isopropyl, hydroxyl, amino, ethylamino, trifluoromethyl, cyano and halogen; and $X^1$ and $Y^1$ are independently selected from CH and N.

Just as a few non-limiting examples of pyrimidine analogues, can be named substituted uracils with the formula (IV) wherein $X^1$ is CH, $R^7$ is hydroxyl, and $R^8$ is selected from the group consisting of methyl, ethyl, isopropyl, amino, ethylamino, trifluoromethyl, cyano, fluoro, chloro, bromo and iodo.

The term "alkyl" as used herein refers to a straight (normal) or branched (eg. secondary, or tertiary) hydrocarbon chains having the number of carbon atoms as indicated (or where not indicated, preferably having 1-20, more preferably 1-6 carbon atoms). The term "$C_1$-$C_6$ alkyl" refers to such hydrocarbon chains having from 1 to 6 carbon atoms. Examples thereof are methyl, ethyl, 1-propyl, 2-propyl, 1-butyl, 2-methyl-1-propyl(i-Bu), 2-butyl (s-Bu) 2-methyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, n-pentyl, n-hexyl.

As used herein with respect to a substituting radical, and unless otherwise stated, the term "$C_2$-$C_{10}$ alkenyl" designate a straight and branched acyclic hydrocarbon monovalent radical having one or more ethylenic unsaturations and having from 2 to 10 carbon atoms such as, for example, vinyl, 1-propenyl, 2-propenyl (allyl), 1-butenyl, 2-butenyl, 2-pentenyl, 3-pentenyl, 3-methyl-2-butenyl, 3-hexenyl, 2-hexenyl, 2-heptenyl, 1,3-butadienyl, pentadienyl, hexadienyl, heptadienyl, heptatrienyl, 2-octenyl and the like, including all possible isomers thereof.

As used herein with respect to a substituting radical, and unless otherwise stated, the term "$C_2$-$C_{10}$ alkynyl" defines straight and branched chain hydrocarbon radicals containing one or more triple bonds and optionally at least one double bond and having from 2 to 10 carbon atoms such as, for example, acetylenyl, 1-propynyl, 2-propynyl, 1-butynyl, 2-butynyl, 2-pentynyl, 1-pentynyl, 3-methyl-2-butynyl, 3-hexynyl, 2-hexynyl, 1-penten-4-ynyl, 3-penten-1-ynyl, 1,3-hexadien-1-ynyl and the like.

As used herein and unless otherwise stated, the term "cycloalkyl" means a monocyclic saturated hydrocarbon monovalent radical having the number of carbon atoms as indicated (or where not indicated, preferably having 3-20, more preferably 3-10 carbon atoms, more preferably 3-8 or 3-6 carbon atoms). "$C_3$-$C_8$ cycloalkyl" refers to such monocyclic saturated hydrocarbon monovalent radical having from 3 to 8 carbon atoms, such as for instance cyclopropyl, cyclobutyl, cyclopentyl, cyclohexyl, cycloheptyl, cyclooctyl.

The term "alkoxy" refers to the group alkyl-O—, where alkyl is as defined above. "($C_1$-$C_6$) alkoxy" as used herein includes but is not limited to methoxy, ethoxy, propoxy, isopropoxy, butoxy, iso-butoxy, sec-butoxy, pentoxy, 3-pentoxy, or hexyloxy.

As used herein and unless otherwise stated, the term "halogen" or "halo" means any atom selected from the group consisting of fluorine (F), chlorine ($C_1$), bromine (Br) and iodine (I).

As used herein and unless otherwise stated, the term "Ar" or "aryl" means a monovalent unsaturated aromatic carbocyclic radical having one, two, three, four, five or six rings, preferably one, two or three rings, which may be fused or bicyclic. An aryl group may optionally be substituted by one, two, three or more substituents as set out in this invention with respect to optional substituents that may be present on the group Ar or aryl. Preferred aryl groups are: an aromatic monocyclic ring containing 6 carbon atoms; an aromatic bicyclic or fused ring system containing 7, 8, 9 or 10 carbon atoms; or an aromatic tricyclic ring system containing 10, 11, 12, 13 or 14 carbon atoms. Non-limiting examples of aryl include phenyl and naphthyl. Preferred substituent groups of Ar are independently selected from halogen, $C_1$-$C_6$ alkyl, $C_1$-$C_6$ alkoxy, hydroxy (—OH), acyl (R'—C(=O)—), acyloxy (R'—C(=O)—O—), nitro (—$NO_2$), amino (—$NH_2$), —$SO_3H$, —SH, —SR', wherein R' is an alkyl. Preferred Ar are phenyl, bromophenyl and naphthyl.

As used herein and unless otherwise stated, the term "stereoisomer" refers to all possible different isomeric as well as conformational forms which the compounds of formula Ia and Ib may possess, in particular all possible stereochemical and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

EXAMPLES

Experimental Section

For reactions, all reagents and solvents were purchased from commercial sources and were used as obtained. Moisture sensitive reactions were carried out in oven-dried glassware under a nitrogen or argon atmosphere. $^1H$, $^{13}C$, and $^{31}P$ NMR spectra were recorded on Bruker Avance 300, 500, or 600 MHz spectrometers with tetramethylsilane as internal standard or referenced to the residual solvent signal, and 85% $H_3PO_4$ for $^{31}P$ NMR experiments. The intermediates and final compounds were characterized by using 2D NMR (H—COSY, HSQC, and HMBC) spectroscopic techniques. High-resolution mass spectra (HRMS) were obtained on a quadruple orthogonal acceleration time-of-flight mass spectrometer (Synapt G2 HDMS, Waters, Milford, Mass.). Samples were infused at 3 μL/min, and spectra were obtained in positive (or in negative) ionization mode with a resolution of 15 000 (fwhm) using leucine enkephalin as the lock mass. Pre-coated aluminum sheets (254 nm) were used for TLC. Products were purified by column chromatography on silica gel (60 Å, 0.035-0.070 mm, Acros Organics). Preparative RP-HPLC purifications were performed on a Phenomenex Gemini 110A column (C18, 10 μm, 21.2 mm×250 mm) using $H_2O/CH_3CN$ with 50 mmol TEAB or $H_2O/CH_3CN$ as eluent gradient.

Examples 1-7: Synthesis of Amino Acid Esters

General Procedure

To a suspension of an amino acid (1 eq.) in anhydrous amyl alcohol, thionyl chloride (10 eq.) was added dropwise at 0° C. under an argon atmosphere. The mixture was allowed to come to room temperature and stirred for 12 h. The suspension was then refluxed for 5 h. After evaporation, the residue was redissolved in petroleum ether. This solution was kept in −20° C. for 12 h and the supernatant was tipped to get the precipitate as a white powder.

The following compounds were synthesized according to this procedure:

Example 1: Amyl Ester of L-Phenylalanine HCl Salt

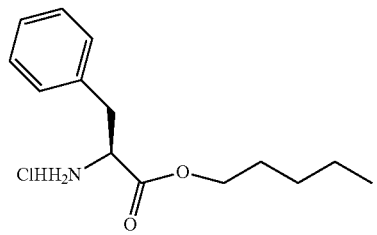

Amyl ester of L-phenylalanine HCl salt was obtained as a white powder (700 mg, 85%) according to the general procedure, starting from L-phenylalanine (500 mg, 3.00 mmol) and thionyl chloride (2.2 mL, 30.27 mmol) in anhydrous amyl alcohol (10 mL). $^1H$ NMR (300 MHz, DMSO-$d_6$): δ 8.86 (s, 3H, $NH_3^+$), 7.33-7.24 (m, 5H, ArH), 4.19 (dd, J=8.4, 5.3 Hz, 1H, Phe-CH), 4.00 (t, J=6.5 Hz, 2H, $OCH_2$($CH_2$)$_3CH_3$), 3.28 (dd, J=13.9, 5.2 Hz, 1H, Phe-$CH_2$a), 3.06 (dd, J=13.9, 8.4 Hz, 1H, Phe-$CH_2$b), 1.47-1.37 (m, 2H, $OCH_2CH_2$($CH_2$)$_2CH_3$), 1.25-1.05 (m, 4H, $O(CH_2)_2(CH_2)_2CH_3$), 0.83 (t, J=7.1 Hz, 3H, $O(CH_2)_4CH_3$); $^{13}C$ NMR (300 MHz, DMSO-$d_6$): 169.1 (Phe-CO), 135.0 (Ar—C), 129.5 (Ar—C), 128.6 (Ar—C), 127.3 (Ar—C), 65.5 ($OCH_2$($CH_2$)$_3$ $CH_3$), 53.4 (Phe-CH), 36.1 (Phe-$CH_2$), 27.6, 27.4 ($OCH_2$($CH_2$)$_2CH_2CH_3$), 21.8 ($O(CH_2)_3CH_2CH_3$), 13.9 ($O(CH_2)_4CH_3$); HRMS for $C_{14}H_{21}NO_2$ $[M+H]^+$ calcd.: 236.1645, found: 236.1646.

Example 2: Amyl Ester of L-Methionine HCl Salt

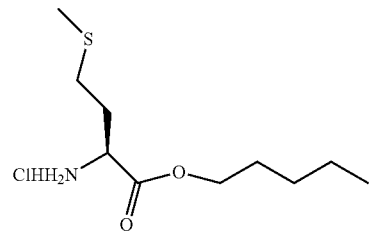

Amyl ester of L-methionine HCl salt was obtained as a white powder (600 mg, 70%) according to the general procedure, starting from L-methionine (500 mg, 3.35 mmol) and thionyl chloride (2.44 mL, 33.50 mmol) in anhydrous amyl alcohol (10 mL). $^1H$ NMR (300 MHz, DMSO-$d_6$): δ 8.78 (s, 3H, $NH_3^+$), 4.18-4.05 (m, 3H, $OCH_2$($CH_2$)$_3CH_3$, Met-CH($CH_2$)$_2SCH_3$), 2.73-2.48 (m, 2H, Met-$CHCH_2CH_2SCH_3$), 2.14-2.02 (m, 5H, Met-$CHCH_2CH_2SCH_3$, Met-$CHCH_2CH_2SCH_3$), 1.64-1.58 (m, 2H, $OCH_2CH_2$($CH_2$)$_2CH_3$), 1.36-1.25 (m, 4H, $O(CH_2)_2$($CH_2$)$_2CH_3$), 0.90-0.84 (m, 3H, $O(CH_2)_4CH_3$); $^{13}C$ NMR (300 MHz, DMSO-$d_6$): 169.3 (Met-CO), 65.8 ($OCH_2$($CH_2$)$_3$ CH$_3$), 51.0 (Met-CH(CH$_2$)$_2$SCH$_3$), 29.6 (Met-CHCH$_2$CH$_2$SCH$_3$), 28.6 (Met-CHCH$_2$CH$_2$SCH$_3$), 27.7, 27.5 (OCH$_2$(CH$_2$)$_2$CH$_2$CH$_3$), 21.8 (O(CH$_2$)$_3$CH$_2$CH$_3$), 14.4 (Met-CH(CH$_2$)$_2$SCH$_3$), 13.9 (O(CH$_2$)$_4$CH$_3$); HRMS for C$_{10}$H$_{21}$NO$_2$S [M+H]$^+$ calcd.: 220.1336, found: 220.1367.

Example 3: Amyl Ester of L-Alanine HCl Salt

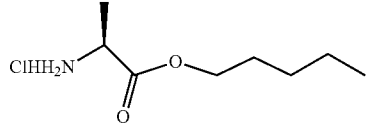

Amyl ester of L-alanine HCl salt was obtained as a white powder (900 mg, 90%) according to the general procedure, starting from L-alanine (500 mg, 5.61 mmol) and thionyl chloride (4.07 mL, 56.10 mmol) in anhydrous amyl alcohol (10 mL). $^1$H NMR (300 MHz, DMSO-d$_6$): δ 8.75 (s, 3H, NH$_3^+$), 4.17-3.97 (m, 3H, OCH$_2$(CH$_2$)$_3$CH$_3$, Ala-CH), 1.64-1.55 (m, 2H, OCH$_2$CH$_2$(CH$_2$)$_2$CH$_3$), 1.44-1.41 (m, 3H, Ala-CH$_3$), 1.35-1.25 (m, 4H, O(CH$_2$)$_2$(CH$_2$)$_2$CH$_3$), 0.88-0.84 (m, 3H, O(CH$_2$)$_4$CH$_3$); $^{13}$C NMR (300 MHz, DMSO-d$_6$): 170.0 (Ala-CO), 65.6 (OCH$_2$(CH$_2$)$_3$CH$_3$), 48.0 (Ala-CH), 27.8, 27.5 (OCH$_2$(CH$_2$)$_2$CH$_2$CH$_3$), 21.8 (O(CH$_2$)$_3$CH$_2$CH$_3$), 15.8 (Ala-CH$_3$), 13.9 (O(CH$_2$)$_4$CH$_3$); HRMS for C$_8$H$_{17}$NO$_2$ [M+H]$^+$ calcd.: 160.1332, found: 160.1332.

Example 4: Amyl Ester of L-Glumatic Acid HCl Salt

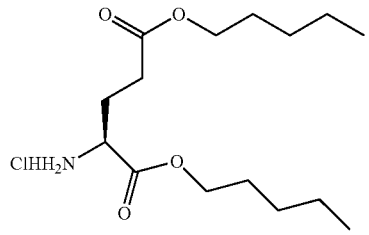

Amyl ester of L-glumatic acid HCl salt was obtained as a white powder (1.30 g, 60%) according to the general procedure, starting from L-glumatic acid (1.00 g, 6.80 mmol) and thionyl chloride (4.94 mL, 67.97 mmol) in anhydrous amyl alcohol (20 mL). $^1$H NMR (300 MHz, DMSO-d$_6$): δ 8.76 (s, 3H, NH$_3^+$), 4.16-4.01 (m, 5H, 2×OCH$_2$(CH$_2$)$_3$CH$_3$, Glu-H-α), 2.62-2.43 (m, 2H, Glu-H-γ, overlapped with DMSO), 2.11-2.04 (m, 2H, Glu-H-β), 1.65-1.52 (m, 4H, 2×OCH$_2$CH$_2$(CH$_2$)$_2$CH$_3$), 1.40-1.22 (m, 8H, 2×O(CH$_2$)$_2$(CH$_2$)$_2$CH$_3$), 0.90-0.85 (m, 6H, 2×O(CH$_2$)$_4$CH$_3$); $^{13}$C NMR (300 MHz, DMSO-d$_6$): 171.8 (Glu-CO-γ), 169.2 (Glu-CO-α), 65.8, 64.3 (OCH$_2$(CH$_2$)$_3$CH$_3$), 51.3 (Glu-C-α), 29.3 (Glu-C-γ), 27.9, 27.2, 27.5 (OCH$_2$(CH$_2$)$_2$CH$_2$CH$_3$), 25.4 (Glu-C-β), 21.9, 21.8 (O(CH$_2$)$_3$CH$_2$CH$_3$), 13.9 (O(CH$_2$)$_4$CH$_3$); HRMS for C$_{15}$H$_{29}$NO$_4$ [M+H]$^+$ calcd.: 288.2169, found: 288.2183.

Example 5: Amyl Ester of L-Valine Acid HCl Salt

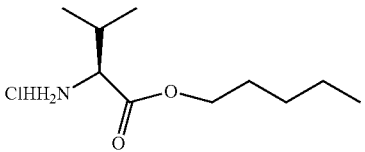

Amyl ester of L-valine acid HCl salt was obtained as a white powder (1.20 g, 63%) according to the general procedure, starting from L-valine (1.00 g, 8.54 mmol) and thionyl chloride (6.00 mL, 85.40 mmol) in anhydrous amyl alcohol (20 mL). $^1$H NMR (300 MHz, DMSO-d$_6$): δ 8.72 (s, 3H, NH$_3^+$), 4.18-4.10 (m, 2H, OCH$_2$(CH$_2$)$_3$CH$_3$), 3.77 (t, J=3.4 Hz, 1H, Val-CHCH(CH$_3$)$_2$), 2.28-2.17 (m, 1H, Val-CHCH(CH$_3$)$_2$), 1.63-1.56 (m, 2H, OCH$_2$CH$_2$(CH$_2$)$_2$CH$_3$), 1.34-1.26 (m, 4H, O(CH$_2$)$_2$(CH$_2$)$_2$CH$_3$), 1.01-0.84 (O(CH$_2$)$_4$ CH$_3$, Val-CHCH(CH$_3$)$_2$); $^{13}$C NMR (300 MHz, DMSO-d$_6$): 168.8 (Val-CO), 65.5 (OCH$_2$(CH$_2$)$_3$CH$_3$), 57.5 (Val-CHCH(CH$_3$)$_2$), 29.4 (Val-CHCH(CH$_3$)$_2$), 27.8, 27.5 (OCH$_2$(CH$_2$)$_2$CH$_2$CH$_3$), 21.8 (O(CH$_2$)$_3$CH$_2$CH$_3$), 18.7, 18.6 (Val-CHCH(CH$_3$)$_2$), 13.9 (O(CH$_2$)$_4$CH$_3$); HRMS for C$_{10}$H$_{21}$NO$_2$ [M+H]$^+$ calcd.: 188.1645, found: 188.1647.

Example 6: Amyl Ester of L-Leucine Acid HCl Salt

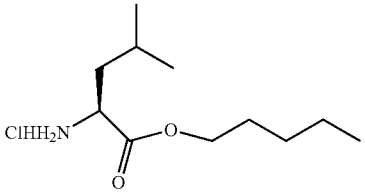

Amyl ester of L-leucine acid HCl salt was obtained as a white powder (1.08 g, 60%) according to the general procedure, starting from L-leucine (1.00 g, 7.62 mmol) and thionyl chloride (5.53 mL, 76.23 mmol) in anhydrous amyl alcohol (20 mL). $^1$H NMR (300 MHz, DMSO-d$_6$): δ 8.71 (s, 3H, NH$_3^+$), 4.14 (t, J=6.6 Hz, 2H, OCH$_2$(CH$_2$)$_3$CH$_3$), 3.88 (t, J=7.0 Hz, 1H, Leu-CHCH$_2$CH(CH$_3$)$_2$), 1.82-1.56 (m, 5H, Leu-CHCH$_2$CH(CH$_3$)$_2$, OCH$_2$CH$_2$(CH$_2$)$_2$CH$_3$, Leu-CHCH$_2$CH(CH$_3$)$_2$), 1.33-1.29 (m, 4H, O(CH$_2$)$_2$(CH$_2$)$_2$CH$_3$), 0.91-0.85 (O(CH$_2$)$_4$CH$_3$, Leu-CHCH$_2$CH(CH$_3$)$_2$); $^{13}$C NMR (300 MHz, DMSO-d$_6$): 170.0 (Leu-CO), 65.6 (OCH$_2$(CH$_2$)$_3$CH$_3$), 50.6 (Leu-CHCH$_2$CH(CH$_3$)$_2$), 40.0 (Leu-CHCH$_2$CH(CH$_3$)$_2$, overlapped with DMSO), 27.7, 27.5 (OCH$_2$(CH$_2$)$_2$CH$_2$CH$_3$), 23.9 (Leu-CHCH$_2$CH(CH$_3$)$_2$), 22.4, 22.0 (Leu-CHCH$_2$CH(CH$_3$)$_2$), 21.8 (O(CH$_2$)$_3$CH$_2$CH$_3$), 13.9 (O(CH$_2$)$_4$CH$_3$); HRMS for C$_{11}$H$_{23}$NO$_2$ [M+H]$^+$ calcd.: 202.1802, found: 202.1804.

Example 7: Amyl Ester of L-Isoleucine Acid HCl Salt

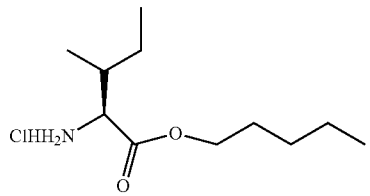

Amyl ester of L-isoleucine acid HCl salt was obtained as a colorless oil (1.26 g, 70%) according to the general procedure, starting from L-isoleucine (1.00 g, 7.62 mmol) and thionyl chloride (5.53 mL, 76.23 mmol) in anhydrous amyl alcohol (20 mL). $^1$H NMR (300 MHz, DMSO-$d_6$): δ 8.72 (s, 3H, $NH_3^+$), 4.19-4.09 (m, 2H, $OCH_2(CH_2)_3CH_3$), 3.86 (d, J=3.6 Hz, 1H, Ile-CHCH($CH_3$)$CH_2CH_3$), 2.00-1.94 (m, 1H, Ile-CHCH($CH_3$)$CH_2CH_3$), 1.65-1.56 (m, 2H, $OCH_2CH_2(CH_2)_2CH_3$), 1.50-1.28 (m, 6H, Ile-CHCH($CH_3$)$CH_2CH_3$, $O(CH_2)_2(CH_2)_2CH_3$), 0.91-0.86 (m, 9H, $O(CH_2)_4CH_3$, Ile-CHCH($CH_3$)$CH_2CH_3$); $^{13}$C NMR (300 MHz, DMSO-$d_6$): 168.7 (Ile-CO), 65.5 ($OCH_2(CH_2)_3CH_3$), 56.1 (Ile-CHCH($CH_3$)$CH_2CH_3$), 36.0 (Ile-CHCH($CH_3$)$CH_2CH_3$), 27.8, 27.6 ($OCH_2(CH_2)_2CH_2CH_3$), 25.6 (Ile-CHCH($CH_3$)$CH_2CH_3$), 21.8 ($O(CH_2)_3CH_2CH_3$), 14.4 (Ile-CHCH($CH_3$)$CH_2CH_3$), 13.9 ($O(CH_2)_4CH_3$), 11.6 (Ile-CHCH($CH_3$)$CH_2CH_3$); HRMS for $C_{11}H_{23}NO_2$ $[M+H]^+$ calcd.: 202.1802, found: 202.1804.

Examples 8-18: Synthesis of Phosphonoamidate Prodrugs of cHPMPA and cHPMPC

General Procedure

The relevant phosphonic acid (1 eq.) was mixed with amino acid ester HCl salt (1.7 eq.) and phenol (4.4 eq.) in anhydrous pyridine. Then $Et_3N$ (10 eq.) was added and the mixture was stirred at 60° C. under a nitrogen atmosphere for 15-20 min. 2,2'-dithiodipyridine (7 eq.) was mixed in a separate flask with $PPh_3$ (7 eq.) in anhydrous pyridine and the resultant mixture was stirred for 10-15 min to give a clear light yellow solution. This solution was then added to the above solution and the combined mixture was stirred at 60° C. for 12 h. The mixture was then concentrated under reduced pressure to give a residue that was redissolved in EtOAc. This solution was washed with saturated aq. $NaHCO_3$ and brine, the organic layer was separated, dried over $Na_2SO_4$, filtered, and concentrated under reduced pressure. The crude residue was purified by silica gel chromatography to give the desired phosphonamidate. The residue was redissolved in DCM/TCA (6%) (1:1, v/v) at room temperature and stirred for 2 h. The reaction was quenched with $Et_3N$. After removal of all the volatiles, the residue was redissolved in EtOAc. This solution was washed with saturated aq. $NaHCO_3$ and brine, the organic layer was separated, dried over $Na_2SO_4$, filtered, and concentrated under reduced pressure. The resulting residue was purified by column chromatography on silica gel (DCM and MeOH) and then purified by RP-HPLC (linear gradient, 5-95% $CH_3CN$ in water) to give desired prodrugs.

Example 8: Diamyl {(5S)-5-[(6-amino-9H-purin-9-yl)methyl]-2-oxido-1,4,2-dioxaphosphinan-2-yl}-L-aspartate (4a)

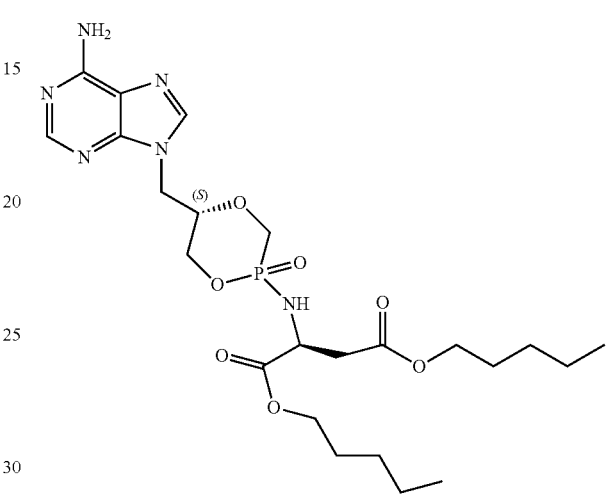

Compound 4a was obtained as a white powder (20 mg, 42%) according to the general procedure, starting from compound 1a (60 mg, 0.089 mmol, $Et_3N$ salt), L-aspartic acid amyl diester HCl salt (47 mg, 0.15 mmol), PhOH (37 mg, 0.39 mmol), $Et_3N$ (0.10 mL, 0.89 mmol), 2,2'-dithiodipyridine (130 mg, 0.62 mmol), and $PPh_3$ (160 mg, 0.62 mmol) in anhydrous pyridine (5 mL), and DCM/TCA (6%) (1:1, v/v, 8 mL). The crude residue was purified by column chromatography on silica gel (gradient DCM/MeOH, 25:1, v/v; 20:1, v/v; 10:1, v/v). $^1$H NMR (300 MHz, MeOD): δ 8.22, 8.21 (s, 1H, H-2), 8.09, 8.07 (s, 1H, H-8), 4.49-3.85 (m, 12H, H-1', H-2', H-3', 2×$OCH_2(CH_2)_3CH_3$, $PCH_2$, Asp-H-α), 2.85-2.75 (m, 2H, Asp-H-β), 1.63-1.61 (m, 4H, 2×$OCH_2CH_2(CH_2)_2CH_3$), 1.37-1.31 (m, 8H, 2×$O(CH_2)_2(CH_2)_2CH_3$), 0.95-0.88 (m, 6H, 2×$O(CH_2)_4CH_3$); $^{13}$C NMR (75 MHz, MeOD): δ 173.4 (d, $^3J_{C,P}$=4.0 Hz, Asp-CO-α), 173.2 (d, $^3J_{C,P}$=3.3 Hz, Asp-CO-α), 172.1, 172.0 (Asp-CO-β), 157.3 (C-6), 153.9 (C-2), 150.9, 150.7 (C-4), 143.5, 143.1 (C-8), 119.8 (C-5), 75.2 (d, $^3J_{C,P}$=4.3 Hz, C-2'), 74.7 (d, $^3J_{C,P}$=4.9 Hz, C-2'), 71.2 (d, $^2J_{C,P}$=8.2 Hz, C-3'), 71.1 (d, $^2J_{C,P}$=6.7 Hz, C-3'), 67.4 (d, $^1J_{C,P}$=127.5 Hz, $CH_2P$), 66.9, 66.2 ($OCH_2(CH_2)_3CH_3$), 65.6 (d, $^1J_{C,P}$=120.0 Hz, $CH_2P$), 51.6, 51.5 (Asp-C-α), 44.3, 44.2 (C-1'), 39.7 (Asp-C-β), 29.4, 29.3, 29.2, 29.1 ($OCH_2(CH_2)_2CH_2CH_3$), 23.4, 23.3 ($O(CH_2)_3CH_2CH_3$), 14.3 ($O(CH_2)_4CH_3$); $^{31}$P NMR (121 MHz, MeOD): δ 17.7, 16.9; HRMS for $C_{23}H_{37}N_6O_7P$ $[M+H]^+$ calcd.: 541.2534, found: 541.2534.

Example 9: Diamyl {(5R)-5-[(6-amino-9H-purin-9-yl)methyl]-2-oxido-1,4,2-dioxaphosphinan-2-yl}-L-aspartate (4b)

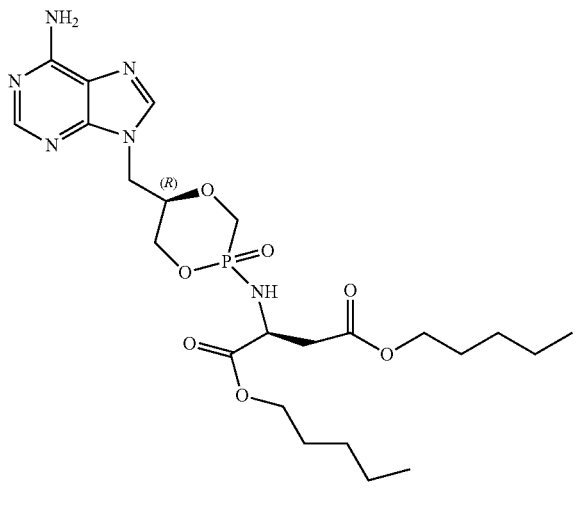

Compound 4b was obtained as a white powder (18 mg, 37%) according to the general procedure, starting from compound 1b (60 mg, 0.089 mmol, Et$_3$N salt), L-aspartic acid amyl diester HCl salt (47 mg, 0.15 mmol), PhOH (37 mg, 0.39 mmol), Et$_3$N (0.10 mL, 0.89 mmol), 2,2'-dithiodipyridine (130 mg, 0.62 mmol), and PPh$_3$ (160 mg, 0.62 mmol) in anhydrous pyridine (5 mL), and DCM/TCA (6%) (1:1, v/v, 8 mL). The crude residue was purified by column chromatography on silica gel (gradient DCM/MeOH, 25:1, v/v; 20:1, v/v; 10:1, v/v). $^1$H NMR (300 MHz, MeOD): δ 8.23 (s, 1H, H-2), 8.10 (s, 1H, H-8), 4.48-3.85 (m, 12H, H-1', H-2', H-3', 2×OCH$_2$(CH$_2$)$_3$CH$_3$, PCH$_2$, Asp-H-α), 2.86-2.76 (m, 2H, Asp-H-β), 1.66-1.59 (m, 4H, 2×OCH$_2$CH$_2$(CH$_2$)$_2$CH$_3$), 1.38-1.31 (m, 8H, 2×O(CH$_2$)$_2$(CH$_2$)$_2$CH$_3$), 0.96-0.89 (m, 6H, 2×O(CH$_2$)$_4$CH$_3$); $^{13}$C NMR (75 MHz, MeOD): δ 173.6 (d, $^3J_{C,P}$=3.1 Hz, Asp-CO-α), 173.3 (d, $^3J_{C,P}$=3.2 Hz, Asp-CO-α), 172.1, 172.0 (Asp-CO-β), 157.3 (C-6), 153.8 (C-2), 150.9, 150.7 (C-4), 143.5, 143.2 (C-8), 119.8 (C-5), 75.2 (d, $^3J_{C,P}$=4.3 Hz, C-2'), 74.7 (d, $^3J_{C,P}$=4.8 Hz, C-2'), 71.3 (d, $^2J_{C,P}$=6.8 Hz, C-3'), 71.2 (d, $^2J_{C,P}$=6.3 Hz, C-3'), 67.7 (d, $^1J_{C,P}$=135.0 Hz, CH$_2$P), 66.9, 66.2 (OCH$_2$(CH$_2$)$_3$CH$_3$), 65.7 (d, $^1J_{C,P}$=127.5 Hz, CH$_2$P), 51.7, 50.9 (Asp-C-α), 44.4, 44.3 (C-1'), 39.8 (d, $^3J_{C,P}$=5.4 Hz, Asp-C-β), 39.3 (d, $^3J_{C,P}$=6.0 Hz, Asp-C-β), 29.4, 29.3, 29.2, 29.1 (OCH$_2$(CH$_2$)$_2$CH$_2$CH$_3$), 23.4, 23.3 (O(CH$_2$)$_3$CH$_2$CH$_3$), 14.3 (O(CH$_2$)$_4$CH$_3$); $^{31}$P NMR (121 MHz, MeOD): δ 17.8, 17.4; HRMS for C$_{23}$H$_{37}$N$_6$O$_7$P [M+H]$^+$ calcd.: 541.2534, found: 541.2527.

Example 10: Diamyl {(5S)-5-[(4-amino-2-oxopyrimidin-1(2H)-yl)methyl]-2-oxido-1,4,2-dioxaphosphinan-2-yl}-L-aspartate (5a)

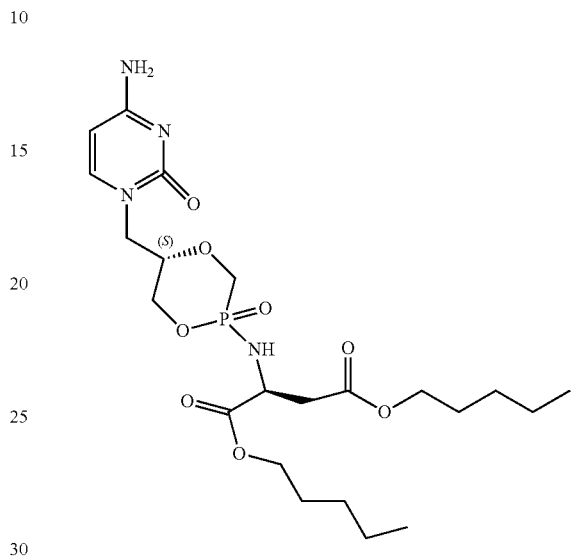

Compound 5a was obtained as a white powder (15 mg, 32%) according to the general procedure, starting from compound 2a (60 mg, 0.092 mmol, Et$_3$N salt), L-aspartic acid amyl diester HCl salt (48 mg, 0.16 mmol), PhOH (38 mg, 0.40 mmol), Et$_3$N (0.10 mL, 0.92 mmol), 2,2'-dithiodipyridine (142 mg, 0.64 mmol), and PPh$_3$ (170 mg, 0.64 mmol) in anhydrous pyridine (5 mL), and in DCM/TCA (6%) (1:1, v/v, 8 mL). The crude residue was purified by column chromatography on silica gel (gradient DCM/MeOH, 15:1, v/v; 10:1, v/v). $^1$H NMR (300 MHz, MeOD): δ 7.51-7.48 (m, 1H, H-6), 5.84-5.81 (m, 1H, H-5), 4.45-3.60 (m, 12H, H-1', H-2', H-3', 2×OCH$_2$(CH$_2$)$_3$CH$_3$, PCH$_2$, Asp-H-α), 2.93-2.71 (m, 2H, Asp-H-β), 1.67-1.61 (m, 4H, 2×OCH$_2$CH$_2$(CH$_2$)$_2$CH$_3$), 1.38-1.31 (m, 8H, 2×O(CH$_2$)$_2$(CH$_2$)$_2$CH$_3$), 0.95-0.90 (m, 6H, 2×O(CH$_2$)$_4$CH$_3$); $^{13}$C NMR (75 MHz, MeOD): δ 173.5, 173.2 (Asp-CO-α), 172.1 (Asp-CO-β), 168.2, 168.1 (C-4), 159.0 (C-2), 148.5, 148.1 (C-4), 95.7, 95.5 (C-5), 75.4 (d, $^3J_{C,P}$=4.2 Hz, C-2'), 75.1 (d, $^3J_{C,P}$=4.9 Hz, C-2'), 71.7 (d, $^2J_{C,P}$=8.8 Hz, C-3'), 71.3 (d, $^2J_{C,P}$=6.8 Hz, C-3'), 67.4 (d, $^1J_{C,P}$=135.0 Hz, CH$_2$P), 66.9, 66.2 (OCH$_2$(CH$_2$)$_3$CH$_3$), 66.1 (d, $^1J_{C,P}$=127.5 Hz, CH$_2$P), 51.6, 51.5 (Asp-C-α), 50.4, 50.1 (C-1'), 39.7 (Asp-C-β), 29.4, 29.3, 29.2, 29.1 (OCH$_2$(CH$_2$)$_2$CH$_2$CH$_3$), 23.3 (O(CH$_2$)$_3$CH$_2$CH$_3$), 14.3 (O(CH$_2$)$_4$CH$_3$); $^{31}$P NMR (121 MHz, MeOD): δ 17.5, 17.1; HRMS for C$_{22}$H$_{37}$N$_4$O$_8$P [M+H]$^+$ calcd.: 517.2422, found: 517.2418.

Example 11: Diamyl {(5R)-5-[(4-amino-2-oxopyrimidin-1(2H)-yl)methyl]-2-oxido-1,4,2-dioxaphosphinan-2-yl}-L-aspartate (5b)

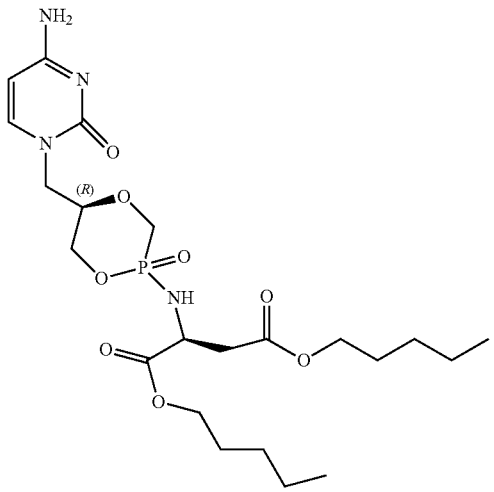

Compound 5b was obtained as a white powder (12 mg, 26%) according to the general procedure, starting from compound 2b (60 mg, 0.092 mmol, Et$_3$N salt), L-aspartic acid amyl diester HCl salt (48 mg, 0.16 mmol), PhOH (38 mg, 0.40 mmol), Et$_3$N (0.10 mL, 0.92 mmol), 2,2'-dithiodipyridine (142 mg, 0.64 mmol), and PPh$_3$ (170 mg, 0.64 mmol) in anhydrous pyridine (5 mL), and in DCM/TCA (6%) (1:1, v/v, 8 mL). The crude residue was purified by column chromatography on silica gel (gradient DCM/MeOH, 15:1, v/v; 10:1, v/v). $^1$H NMR (300 MHz, MeOD): δ 7.53-7.49 (m, 1H, H-6), 5.86-5.83 (m, 1H, H-5), 4.41-3.65 (m, 12H, H-1', H-2', H-3', 2×OCH$_2$(CH$_2$)$_3$CH$_3$, PCH$_2$, Asp-H-α), 2.89-2.82 (m, 2H, Asp-H-β), 1.71-1.61 (m, 4H, 2×OCH$_2$CH$_2$(CH$_2$)$_2$CH$_3$), 1.41-1.33 (m, 8H, 2×O(CH$_2$)$_2$(CH$_2$)$_2$CH$_3$), 0.98-0.91 (m, 6H, 2×O(CH$_2$)$_4$CH$_3$); $^{13}$C NMR (75 MHz, MeOD): δ 173.6, 173.3 (Asp-CO-α), 172.1, 172.0 (Asp-CO-β), 168.2, 168.1 (C-4), 158.9 (C-2), 148.5, 148.0 (C-4), 95.6, 95.5 (C-5), 75.5 (d, $^3J_{C,P}$=4.3 Hz, C-2'), 75.3 (d, $^3J_{C,P}$=4.8 Hz, C-2'), 71.7 (d, $^2J_{C,P}$=8.2 Hz, C-3'), 71.4 (d, $^2J_{C,P}$=6.6 Hz, C-3'), 68.1 (d, $^1J_{C,P}$=134.6 Hz, CH$_2$P), 66.9, 66.2 (OCH$_2$(CH$_2$)$_3$CH$_3$), 66.0 (d, $^1J_{C,P}$=133.5 Hz, CH$_2$P), 51.7, 51.0 (Asp-C-α), 50.5, 50.1 (C-1'), 39.9 (d, $^3J_{C,P}$=5.5 Hz, Asp-C-β), 39.4 (d, $^3J_{C,P}$=6.2 Hz, Asp-C-β), 29.4, 29.3, 29.2, 29.1 (OCH$_2$(CH$_2$)$_2$CH$_2$CH$_3$), 23.3 (O(CH$_2$)$_3$CH$_2$CH$_3$), 14.2 (O(CH$_2$)$_4$CH$_3$); $^{31}$P NMR (121 MHz, MeOD): δ 17.9, 17.2; HRMS for C$_{22}$H$_{37}$N$_4$O$_8$P [M+H]$^+$ calcd.: 517.2422, found: 517.2428.

Example 12: Amyl ((5S)-5-((6-amino-9H-purin-9-yl)methyl)-2-oxido-1,4,2-dioxaphosphinan-2-yl)-L-phenylalaninate (7)

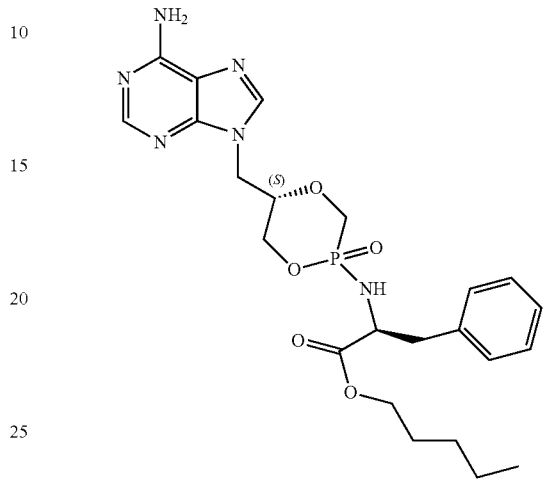

Compound 7 was obtained as a white powder (20 mg, 30%) according to the general procedure, starting from compound 1a (100 mg, 0.15 mmol, Et$_3$N salt), L-phenylalanine amyl ester HCl salt (68 mg, 0.25 mmol), PhOH (61 mg, 0.65 mmol), Et$_3$N (0.15 mL, 1.50 mmol), 2,2'-dithiodipyridine (230 mg, 1.04 mmol), and PPh$_3$ (270 mg, 1.04 mmol) in anhydrous pyridine (5 mL), and in DCM/TCA (6%) (1:1, v/v, 8 mL). The crude residue was purified by column chromatography on silica gel (gradient DCM/MeOH, 15:1, v/v; 10:1, v/v). $^1$H NMR (300 MHz, MeOD): δ 8.24, 8.23 (s, 1H, H-2), 8.07, 8.03 (s, 1H, H-8), 7.29-7.17 (5H, ArH), 4.41-4.01 (m, 7H, H-1', H-2', Phe-CH, H-3'a, OCH$_2$(CH$_2$)$_3$CH$_3$; 0.5H, PCH$_2$a; 0.5H, H-3'b), 3.81-3.71 (m, 0.5H, PCH$_2$a; 0.5H, H-3'b), 3.50-3.28 (m, 1H, PCH$_2$b overlapped with MeOD), 3.17-3.11 (m, 1H, Phe-CH$_2$a), 2.93-2.73 (m, 1H, Phe-CH$_2$b), 1.63-1.59 (m, 2H, OCH$_2$CH$_2$(CH$_2$)$_2$CH$_3$), 1.35-1.30 (m, 4H, O(CH$_2$)$_2$(CH$_2$)$_2$CH$_3$), 0.94-0.89 (m, 3H, O(CH$_2$)$_4$CH$_3$); $^{13}$C NMR (75 MHz, MeOD): δ 174.3 (d, $^3J_{C,P}$=3.2 Hz, Phe-CO), 174.1 (d, $^3J_{C,P}$=3.4 Hz, Phe-CO), 157.4 (C-6), 153.9, 153.8 (C-2), 150.9, 150.7 (C-4), 143.4, 143.1 (C-8), 138.4 (Ar—C), 130.7, 130.5, 12.5, 127.9 (Ar—C), 119.8 (C-5), 75.1 (d, $^3J_{C,P}$=4.3 Hz, C-2'), 74.8 (d, $^3J_{C,P}$=5.0 Hz, C-2'), 71.0, 70.9 (C-3'), 67.1 (d, $^1J_{C,P}$=137.4 Hz, CH$_2$P), 66.5 (OCH$_2$(CH$_2$)$_3$CH$_3$), 65.5 (d, $^1J_{C,P}$=130.7 Hz, CH$_2$P), 56.5, 56.1 (Phe-CH), 44.3, 44.2 (C-1'), 41.3 (d, J=5.0 Hz, Phe-CH$_2$), 41.1 (d, J=6.0 Hz, Phe-CH$_2$), 29.3, 29.1 (OCH$_2$(CH$_2$)$_2$CH$_2$CH$_3$), 23.3 (O(CH$_2$)$_3$CH$_2$CH$_3$), 14.2 (O(CH$_2$)$_4$CH$_3$); $^{31}$P NMR (121 MHz, MeOD): δ 17.0, 16.6; HRMS for C$_{23}$H$_{31}$N$_6$O$_5$P [M+H]$^+$ calcd.: 503.2166, found: 503.2177.

Example 13: Amyl ((5S)-5-((6-amino-9H-purin-9-yl)methyl)-2-oxido-1,4,2-dioxaphosphinan-2-yl)-L-methioninate (8)

Example 14: Amyl ((5S)-5-((6-amino-9H-purin-9-yl)methyl)-2-oxido-1,4,2-dioxaphosphinan-2-yl)-L-alaninate (9)

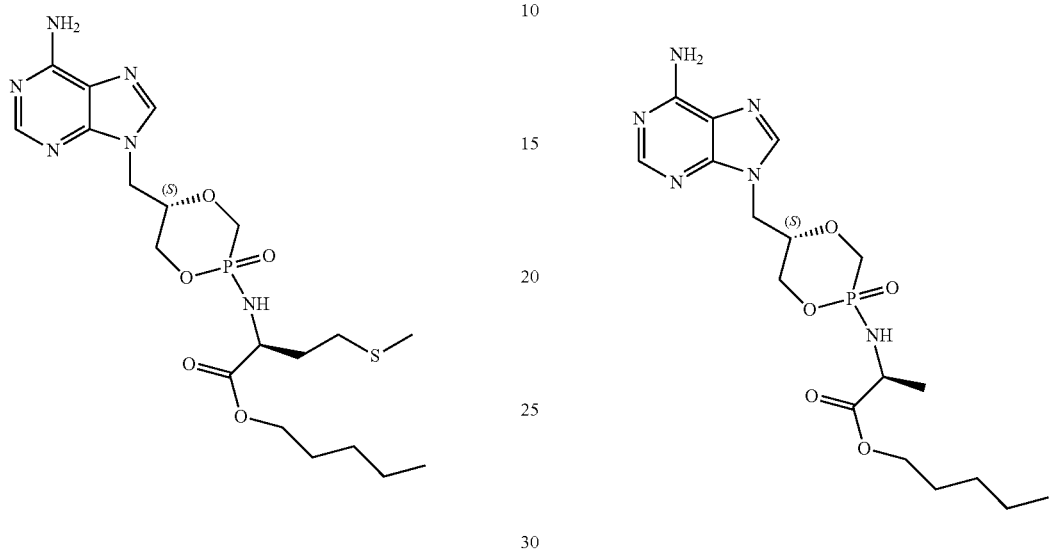

Compound 8 was obtained as a white powder (22 mg, 30%) according to the general procedure, starting from compound 1a (100 mg, 0.15 mmol, Et$_3$N salt), L-methionine amyl ester HCl salt (65 mg, 0.25 mmol), PhOH (61 mg, 0.65 mmol), Et$_3$N (0.15 mL, 1.50 mmol), 2,2'-dithiodipyridine (230 mg, 1.04 mmol), and PPh$_3$ (270 mg, 1.04 mmol) in anhydrous pyridine (5 mL), and in DCM/TCA (6%) (1:1, v/v, 8 mL). The crude residue was purified by column chromatography on silica gel (gradient DCM/MeOH, 15:1, v/v; 10:1, v/v). $^1$H NMR (300 MHz, MeOD): δ 8.24, 8.23 (s, 1H, H-2), 8.12, 8.09 (s, 1H, H-8), 4.56-3.87 (m, 10H, H-1', H-2', H-3', OCH$_2$(CH$_2$)$_3$CH$_3$, PCH$_2$, CHCH$_2$CH$_2$SCH$_3$), 2.62-2.53 (m, 2H, Met-CHCH$_2$CH$_2$SCH$_3$), 2.14-2.02 (m, 5H, Met-CHCH$_2$CH$_2$SCH$_3$, Met-CHCH$_2$CH$_2$SCH$_3$), 1.69-1.62 (m, 2H, OCH$_2$CH$_2$(CH$_2$)$_2$CH$_3$), 1.39-1.31 (m, 4H, O(CH$_2$)$_2$(CH$_2$)$_2$CH$_3$), 0.96-0.88 (m, 3H, O(CH$_2$)$_4$CH$_3$); $^{13}$C NMR (75 MHz, MeOD): δ 174.6, 174.4 (Met-CO), 157.3 (C-6), 153.9 (C-2), 151.0, 150.8 (C-4), 143.5, 143.2 (C-8), 119.8 (C-5), 75.1 (d, $^3J_{C,P}$=4.4 Hz, C-2'), 74.7 (d, $^3J_{C,P}$=4.9 Hz, C-2'), 71.2 (d, $^3J_{C,P}$=8.1 Hz, C-3'), 70.9 (d, $^2J_{C,P}$=6.7 Hz, C-3'), 67.0 (d, $^1J_{C,P}$=136.2 Hz, CH$_2$P), 66.6 (OCH$_2$(CH$_2$)$_3$CH$_3$), 65.6 (d, $^1J_{C,P}$=131.2 Hz, CH$_2$P), 53.8, 53.7 (Met-CH(CH$_2$)$_2$SCH), 44.4, 44.2 (C-1'), 34.2, 34.1 (Met-CHCH$_2$CH$_2$SCH$_3$), 31.1, 31.0 (Met-CHCH$_2$CH$_2$SCH$_3$), 29.4, 29.3, 29.2 (OCH$_2$(CH$_2$)$_2$CH$_2$CH$_3$), 23.3 (O(CH$_2$)$_3$CH$_2$CH$_3$), 15.2, 15.1 (Met-CH(CH$_2$)$_2$SCH$_3$), 14.2 (O(CH$_2$)$_4$CH$_3$); $^{31}$P NMR (121 MHz, MeOD): δ 18.0, 17.0; HRMS for C$_{19}$H$_{31}$N$_6$O$_5$PS [M+H]$^+$ calcd.: 487.1887, found: 487.1885.

Compound 9 was obtained as a white powder (22 mg, 28%) according to the general procedure, starting from compound 1a (100 mg, 0.15 mmol, Et$_3$N salt), L-alanine amyl ester HCl salt (50 mg, 0.25 mmol), PhOH (61 mg, 0.65 mmol), Et$_3$N (0.15 mL, 1.50 mmol), 2,2'-dithiodipyridine (230 mg, 1.04 mmol), and PPh$_3$ (270 mg, 1.04 mmol) in anhydrous pyridine (5 mL), and in DCM/TCA (6%) (1:1, v/v, 8 mL). The crude residue was purified by column chromatography on silica gel (gradient DCM/MeOH, 15:1, v/v; 10:1, v/v). $^1$H NMR (300 MHz, MeOD): δ 8.24, 8.23 (s, 1H, H-2), 8.12, 8.09 (s, 1H, H-8), 4.51-3.85 (m, 10H, H-1', H-2', H-3', OCH$_2$(CH$_2$)$_3$CH$_3$, PCH$_2$, Ala-CH), 1.69-1.59 (m, 2H, OCH$_2$CH$_2$(CH$_2$)$_2$CH$_3$), 1.44-1.31 (m, 7H, O(CH$_2$)$_2$(CH$_2$)$_2$CH$_3$, Ala-CH$_3$), 0.95-0.86 (m, 3H, O(CH$_2$)$_4$CH$_3$); $^{13}$C NMR (75 MHz, MeOD): δ 175.3, 175.1 (Ala-CO), 157.4 (C-6), 153.9 (C-2), 150.9, 150.8 (C-4), 143.5, 143.2 (C-8), 119.8 (C-5), 75.2 (d, $^3J_{C,P}$=4.2 Hz, C-2'), 74.7 (d, $^3J_{C,P}$=5.1 Hz, C-2'), 71.1 (d, $^3J_{C,P}$=8.0 Hz, C-3'), 70.9 (d, $^2J_{C,P}$=6.7 Hz, C-3'), 67.0 (d, $^1J_{C,P}$=136.4 Hz, CH$_2$P), 66.5 (OCH$_2$(CH$_2$)$_3$CH$_3$), 65.6 (d, $^1J_{C,P}$=130.0 Hz, CH$_2$P), 50.6, 50.4 (Ala-CH), 44.4, 44.3 (C-1'), 29.4, 29.3, 29.1 (OCH$_2$(CH$_2$)$_2$CH$_2$CH$_3$), 23.3 (O(CH$_2$)$_3$CH$_2$CH$_3$), 20.9 (d, $^3J_{C,P}$=5.6 Hz, Ala-CH$_3$), 20.5 (d, $^3J_{C,P}$=6.0 Hz, Ala-CH$_3$), 14.2 (O(CH$_2$)$_4$CH$_3$); $^{31}$P NMR (121 MHz, MeOD): δ 17.9, 16.7; HRMS for C$_{17}$H$_{27}$N$_6$O$_5$P [M+H]$^+$ calcd.: 427.1853, found: 427.1844.

Example 15: Diamyl {(5S)-5-[(6-amino-9H-purin-9-yl)methyl]-2-oxido-1,4,2-dioxaphosphinan-2-yl}-L-glutamate (10)

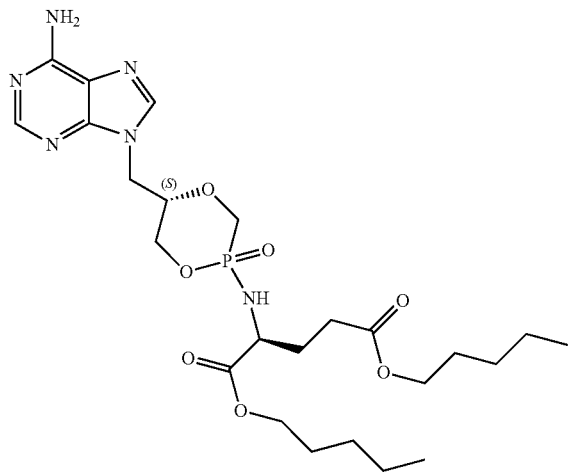

Compound 10 was obtained as a white powder (25 mg, 30%) according to the general procedure, starting from compound 1a (100 mg, 0.15 mmol, Et$_3$N salt), L-glutamic acid amyl diester HCl salt (82 mg, 0.25 mmol), PhOH (61 mg, 0.65 mmol), Et$_3$N (0.15 mL, 1.50 mmol), 2,2'-dithiodipyridine (230 mg, 1.04 mmol), and PPh$_3$ (270 mg, 1.04 mmol) in anhydrous pyridine (5 mL), and in DCM/TCA (6%) (1:1, v/v, 8 mL). The crude residue was purified by column chromatography on silica gel (gradient DCM/MeOH, 15:1, v/v; 10:1, v/v). $^1$H NMR (600 MHz, MeOD): δ 8.20, 8.19 (s, 1H, H-2), 8.08, 8.06 (s, 1H, H-8), 4.55-4.02 (m, 10H, H-1', H-2', H-3', 2×OCH$_2$(CH$_2$)$_3$CH$_3$, PCH$_2$a), 3.98-3.84 (m, 2H, Glu-H-α, PCH$_2$b), 2.47-2.39 (m, 2H, Glu-H-β), 2.17-2.08 (m, 1H, Glu-H-γa), 1.92-1.78 (m, 1H, Glu-H-γb), 1.66-1.57 (m, 4H, 2×OCH$_2$CH$_2$(CH$_2$)$_2$CH$_3$), 1.36-1.27 (m, 8H, 2×O(CH$_2$)$_2$(CH$_2$)$_2$CH$_3$), 0.96-0.84 (m, 6H, 2×O(CH$_2$)$_4$CH$_3$); $^{13}$C NMR (75 MHz, MeOD): δ 174.4 (Glu-CO-α), 174.2, 174.1 (Glu-CO-β), 157.4 (C-6), 153.9 (C-2), 151.0, 150.8 (C-4), 143.4, 143.1 (C-8), 119.8 (C-5), 75.2 (d, $^3J_{C,P}$=4.3 Hz, C-2'), 74.7 (d, $^3J_{C,P}$=5.0 Hz, C-2'), 71.2, 71.1, 71.0, 70.9 (C-3'), 66.9 (d, $^1J_{C,P}$=136.2 Hz, CH$_2$P), 66.6, 65.8 (OCH$_2$(CH$_2$)$_3$CH$_3$), 65.6 (d, $^1J_{C,P}$=131.3 Hz, CH$_2$P), 52.4 (Glu-C-α), 44.3 (C-1'), 31.3, 31.1 (Glu-C-β), 30.0, 29.9, 29.4, 29.3, 29.2, 29.1 (OCH$_2$(CH$_2$)$_2$CH$_2$CH$_3$, Glu-C-β), 23.3 (O(CH$_2$)$_3$CH$_2$CH$_3$), 14.2 (O(CH$_2$)$_4$CH$_3$); $^{31}$P NMR (121 MHz, MeOD): δ 18.0, 16.9; HRMS for C$_{24}$H$_{39}$N$_6$O$_7$P [M−H]$^-$ calcd.: 553.2545, found: 553.2538.

Example 16: Amyl {(5S)-5-[(6-amino-9H-purin-9-yl)methyl]-2-oxido-1,4,2-dioxaphosphinan-2-yl}-L-valinate (11)

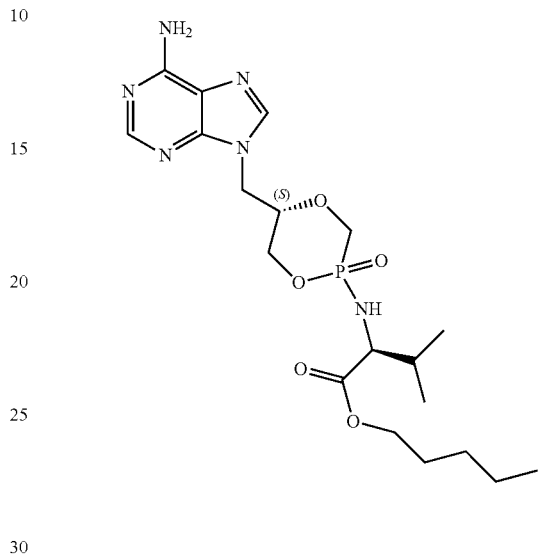

Compound 11 was obtained as a white powder (20 mg, 29%) according to the general procedure, starting from compound 1a (100 mg, 0.15 mmol, Et$_3$N salt), L-valine amyl ester HCl salt (56 mg, 0.25 mmol), PhOH (61 mg, 0.65 mmol), Et$_3$N (0.15 mL, 1.50 mmol), 2,2'-dithiodipyridine (230 mg, 1.04 mmol), and PPh$_3$ (270 mg, 1.04 mmol) in anhydrous pyridine (5 mL), and in DCM/TCA (6%) (1:1, v/v, 8 mL). The crude residue was purified by column chromatography on silica gel (gradient DCM/MeOH, 15:1, v/v; 10:1, v/v). $^1$H NMR (300 MHz, MeOD): δ 8.22 (s, 1H, H-2), 8.10, 8.08 (s, 1H, H-8), 4.54-4.04 (m, 8H, H-1', H-2', H-3', OCH$_2$(CH$_2$)$_3$CH$_3$, PCH$_2$a), 3.91-3.84 (PCH$_2$b), 3.77-3.65 (m, 1H, Val-CHCH(CH$_3$)$_2$), 2.11-2.02 (m, 1H, Val-CHCH(CH$_3$)$_2$), 1.67-1.58 (m, 2H, OCH$_2$CH$_2$(CH$_2$)$_2$CH$_3$), 1.38-1.31 (m, 4H, O(CH$_2$)$_2$(CH$_2$)$_2$CH$_3$), 0.97-0.85 (O(CH$_2$)$_4$CH$_3$, Val-CHCH(CH$_3$)$_2$); $^{13}$C NMR (75 MHz, MeOD): δ174.4 (d, $^3J_{C,P}$=3.6 Hz, Phe-CO), 174.2 (d, $^3J_{C,P}$=2.6 Hz, Phe-CO), 157.4 (C-6), 153.9 (C-2), 151.0, 150.8 (C-4), 143.5 143.2 (C-8), 119.8 (C-5), 75.2 (d, $^3J_{C,P}$=4.3 Hz, C-2'), 74.5 (d, $^3J_{C,P}$=5.0 Hz, C-2'), 71.1, 71.0, 70.9 (C-3'), 66.9 (d, $^1J_{C,P}$=137.1 Hz, CH$_2$P), 66.3 (OCH$_2$(CH$_2$)$_3$CH$_3$), 65.3 (d, $^1J_{C,P}$=131.0 Hz, CH$_2$P), 60.4 (Val-CHCH(CH$_3$)$_2$), 44.4, 44.1 (C-1'), 32.8 (Val-CHCH(CH$_3$)$_2$), 27.8, 27.5 (OCH$_2$(CH$_2$)$_2$CH$_2$CH$_3$), 21.8 (O(CH$_2$)$_3$CH$_2$CH$_3$), 18.7, 18.6 (Val-CHCH(CH$_3$)$_2$), 13.9 (O(CH$_2$)$_4$CH$_3$); HRMS for C$_{10}$H$_{21}$NO$_2$ [M+H]$^+$ calcd.: 188.1645, found: 188.1647. $^{31}$P NMR (121 MHz, MeOD): δ 18.2, 17.3; HRMS for C$_{19}$H$_{31}$N$_6$O$_5$P [M+H]$^+$ calcd.: 455.2166, found: 455.2163.

Example 17: Amyl {(5S)-5-[(6-amino-9H-purin-9-yl)methyl]-2-oxido-1,4,2-dioxaphosphinan-2-yl}-L-leucinate (12)

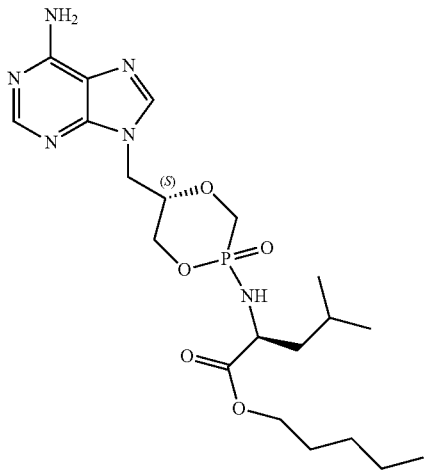

Compound 12 was obtained as a white powder (25 mg, 35%) according to the general procedure, starting from compound 1a (100 mg, 0.15 mmol, Et$_3$N salt), L-leucine amyl ester HCl salt (59 mg, 0.25 mmol), PhOH (61 mg, 0.65 mmol), Et$_3$N (0.15 mL, 1.50 mmol), 2,2'-dithiodipyridine (230 mg, 1.04 mmol), and PPh$_3$ (270 mg, 1.04 mmol) in anhydrous pyridine (5 mL), and in DCM/TCA (6%) (1:1, v/v, 8 mL). The crude residue was purified by column chromatography on silica gel (gradient DCM/MeOH, 15:1, v/v; 10:1, v/v). $^1$H NMR (300 MHz, MeOD): δ 8.22 (s, 1H, H-2), 8.10, 8.08 (s, 1H, H-8), 4.53-4.05 (m, 8H, H-1', H-2', H-3', OCH$_2$(CH$_2$)$_3$CH$_3$, PCH$_2$a), 3.94-3.81 (m, 2H, Leu-CHCH$_2$CH(CH$_3$)$_2$, PCH$_2$b), 1.71-1.31 (m, 5H, Leu-CHCH$_2$CH(CH$_3$)$_2$, OCH$_2$CH$_2$(CH$_2$)$_2$CH$_3$, Leu-CHCH$_2$CH(CH$_3$)$_2$), 1.37-1.31 (m, 4H, O(CH$_2$)$_2$(CH$_2$)$_2$CH$_3$), 0.95-0.87 (O(CH$_2$)$_4$CH$_3$, Leu-CHCH$_2$CH(CH$_3$)$_2$); $^{13}$C NMR (75 MHz, MeOD): δ 175.5, 175.3 (Leu-CO), 157.4 (C-6), 153.9 (C-2), 151.0, 150.8 (C-4), 143.5 143.2 (C-8), 119.9 (C-5), 75.2 (d, $^3J_{C,P}$=4.2 Hz, C-2'), 74.7 (d, $^3J_{C,P}$=5.0 Hz, C-2'), 71.1 (d, $^3J_{C,P}$=8.1 Hz, C-3'), 70.9 (d, $^2J_{C,P}$=6.7 Hz, C-3'), 67.0 (d, $^1J_{C,P}$=136.3 Hz, CH$_2$P), 66.4 (OCH$_2$(CH$_2$)$_3$CH$_3$), 65.7 (d, $^1J_{C,P}$=130.6 Hz, CH$_2$P), 53.4, 53.1 (Leu-CHCH$_2$CH(CH$_3$)$_2$), 44.4, 44.2 (C-1'), 44.1, 44.0, 43.9, 43.8 (Leu-CHCH$_2$CH(CH$_3$)$_2$), 29.4, 29.3, 29.1 (OCH$_2$(CH$_2$)$_2$CH$_2$CH$_3$), 25.7, 25.6 (Leu-CHCH$_2$CH(CH$_3$)$_2$), 23.3 (O(CH$_2$)$_3$CH$_2$CH$_3$), 21.7 (Leu-CHCH$_2$CH(CH$_3$)$_2$), 14.2 (O(CH$_2$)$_4$CH$_3$); $^{31}$P NMR (121 MHz, MeOD): δ 17.8, 16.8; HRMS for C$_{20}$H$_{33}$N$_6$O$_5$P [M+H]$^+$ calcd.: 469.2323, found: 469.2322.

Example 18: Amyl {(5S)-5-[(6-amino-9H-purin-9-yl)methyl]-2-oxido-1,4,2-dioxaphosphinan-2-yl}-L-isoleucinate (13)

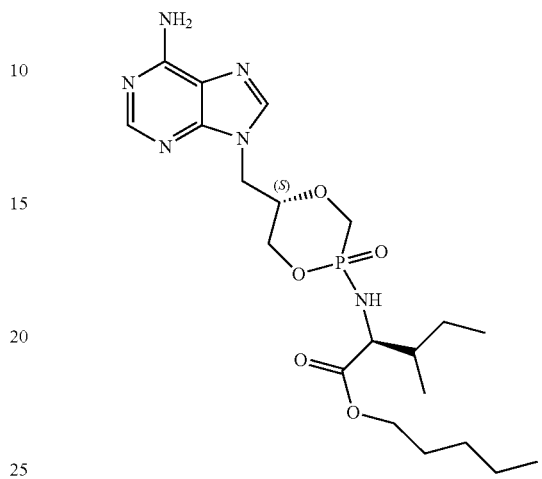

Compound 13 was obtained as a white powder (20 mg, 29%) according to the general procedure, starting from compound 1a (100 mg, 0.15 mmol, Et$_3$N salt), L-isoleucine amyl ester HCl salt (59 mg, 0.25 mmol), PhOH (61 mg, 0.65 mmol), Et$_3$N (0.15 mL, 1.50 mmol), 2,2'-dithiodipyridine (230 mg, 1.04 mmol), and PPh$_3$ (270 mg, 1.04 mmol) in anhydrous pyridine (5 mL), and in DCM/TCA (6%) (1:1, v/v, 8 mL). The crude residue was purified by column chromatography on silica gel (gradient DCM/MeOH, 15:1, v/v; 10:1, v/v). $^1$H NMR (300 MHz, MeOD): δ 8.24 (s, 1H, H-2), 8.12, 8.09 (s, 1H, H-8), 4.51-4.06 (m, 10H, H-1', H-2', H-3', OCH$_2$(CH$_2$)$_3$CH$_3$, PCH$_2$a, Ile-CHCH(CH$_3$)CH$_2$CH$_3$), 3.93-3.72 (m, 2H, PCH$_2$b, Ile-CHCH(CH$_3$)CH$_2$CH$_3$), 1.81 (br, s, 1H, Ile-CHCH(CH$_3$)CH$_2$CH$_3$), 1.66-1.62 (m, 2H, OCH$_2$CH$_2$(CH$_2$)$_2$CH$_3$), 1.48-1.32 (m, 5H, Ile-CHCH(CH$_3$)CH$_2$aCH$_3$, O(CH$_2$)$_2$(CH$_2$)$_2$CH$_3$), 1.19-1.11 (m, 1H, Ile-CHCH(CH$_3$)CH$_2$bCH$_3$), 0.95-0.86 (m, 9H, O(CH$_2$)$_4$CH$_3$, Ile-CHCH(CH$_3$)CH$_2$CH$_3$, Ile-CHCH(CH$_3$)CH$_2$CH$_3$); $^{13}$C NMR (75 MHz, MeOD): δ 174.4 (d, $^3J_{C,P}$=3.4 Hz, Ile-CO), 174.3 (d, $^3J_{C,P}$=2.7 Hz, Ile-CO), 157.4 (C-6), 153.9 (C-2), 151.0, 150.8 (C-4), 143.5, 143.2 (C-8), 119.9, 119.8 (C-5), 75.2 (d, $^3J_{C,P}$=4.3 Hz, C-2'), 74.5 (d, $^3J_{C,P}$=5.2 Hz, C-2'), 71.1, 71.0, 70.9 (C-3'), 66.9 (d, $^1J_{C,P}$=137.1 Hz, CH$_2$P), 66.3 (OCH$_2$(CH$_2$)$_3$CH$_3$), 65.3 (d, $^1J_{C,P}$=130.9 Hz, CH$_2$P), 59.4 (Ile-CHCH(CH$_3$)CH$_2$CH$_3$), 44.4, 44.1 (C-1'), 39.8, 39.7 (Ile-CHCH(CH$_3$)CH$_2$CH$_3$), 29.4, 29.2 (OCH$_2$(CH$_2$)$_2$CH$_2$CH$_3$), 25.9, 25.6 (Ile-CHCH(CH$_3$)CH$_2$CH$_3$), 23.2 (O(CH$_2$)$_3$CH$_2$CH$_3$), 16.0 (Ile-CHCH(CH$_3$)CH$_2$CH$_3$), 14.2 (O(CH$_2$)$_4$CH$_3$), 11.7, 11.6 (Ile-CHCH(CH$_3$)CH$_2$CH$_3$); $^{31}$P NMR (121 MHz, MeOD): δ 18.1, 17.3; HRMS for C$_{20}$H$_{33}$N$_6$O$_5$P [M+H]$^+$ calcd.: 469.2323, found: 469.2320.

Example 19: Synthesis of diamyl 2,2'-((((((S)-1-(6-amino-9H-purin-9-yl)-3-hydroxypropan-2-yl)oxy)methyl)phosphoryl)bis(azanediyl))(2S,2'S)-bis(3-methylbutanoate) (14)

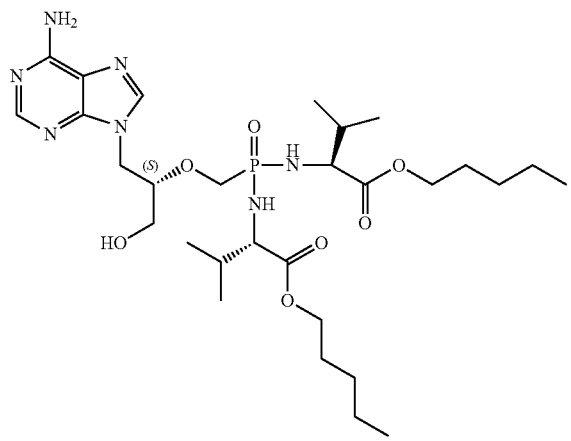

Compound 1a (100 mg, 0.15 mmol, Et$_3$N salt) was mixed with L-valine amyl ester HCl salt (130 mg, 0.59 mmol) in anhydrous pyridine (3 mL). Then Et$_3$N (0.15 mL, 1.50 mmol) was added and the mixture was stirred at 60° C. under a nitrogen atmosphere for 15-20 min. 2,2'-dithiodipyridine (230 mg, 1.04 mmol) was mixed in a separate flask with PPh$_3$ (270 mg, 1.04 mmol) in anhydrous pyridine (3 mL) and the resultant mixture was stirred for 10-15 min to give a clear light yellow solution. This solution was then added to the above solution and the combined mixture was stirred at 60° C. for 12 h. The mixture was then concentrated under reduced pressure to give a residue that was redissolved in EtOAc (100 mL). This solution was washed with saturated aq. NaHCO$_3$ (50 mL) and brine (50 mL), the organic layer was separated, dried over Na$_2$SO$_4$, filtered, and concentrated under reduced pressure. The crude residue was purified by silica gel chromatography to give the desired phosphonamidate. The residue was redissolved in DCM/TCA (6%) (1:1, v/v) at room temperature and stirred for 2 h. The reaction was quenched with Et$_3$N. After removal of all the volatiles, the residue was redissolved in EtOAc (50 mL). This solution was washed with saturated aq. NaHCO$_3$ (50 mL) and brine (50 mL), the organic layer was separated, dried over Na$_2$SO$_4$, filtered, and concentrated under reduced pressure. The resulting residue was purified by column chromatography on silica gel (gradient DCM/MeOH, 15:1, v/v; 10:1, v/v) and then purified by RP-HPLC (linear gradient, 5-95% CH$_3$CN in water) to compound 14 (30 mg, 32%) as a white powder. $^1$H NMR (300 MHz, MeOD): δ 8.24-8.23 (m, 2H, H-2, H-8), 4.54-4.37 (m, 2H, H-1'), 4.24-3.58 (m, 6H, 2×OCH$_2$(CH$_2$)$_3$CH$_3$, PCH$_2$a, H-2'), 3.77-3.58 (m, 5H, PCH$_2$b, 2×Val-CHCH(CH$_3$)$_2$, H-3'), 2.13-2.03 (m, 2H, 2×Val-CHCH(CH$_3$)$_2$), 1.42-1.30 (m, 2H, OCH$_2$CH$_2$(CH$_2$)$_2$CH$_3$), 1.00-0.80 (m, 4H, O(CH$_2$)$_2$(CH$_2$)$_2$CH$_3$), $^{13}$C NMR (75 MHz, MeOD): δ 175.1, 175.0, 174.9 (Val-CO), 157.3 (C-6), 153.7 (C-2), 151.2 (C-4), 143.8 (C-8), 120.0 (C-5), 82.1 (d, $^3J_{C,P}$=11.7 Hz, C-2'), 68.0-66.2 (CH$_2$P, OCH$_2$(CH$_2$)$_3$CH$_3$), 61.5 (C-3'), 60.2, 60.1, 59.3 (Val-CHCH(CH$_3$)$_2$), 45.5 (C-1'), 33.1, 33.0, 32.9 (Val-CHCH(CH$_3$)$_2$), 29.4, 29.3, 29.2 (OCH$_2$(CH$_2$)$_2$CH$_2$CH$_3$), 23.3 (O(CH$_2$)$_3$CH$_2$CH$_3$), 19.7, 19.5, 18.1, 17.8 (Val-CHCH(CH$_3$)$_2$), 14.2 (O(CH$_2$)$_4$CH$_3$); $^{31}$P NMR (121 MHz, MeOD): δ 25.0; HRMS for C$_{29}$H$_{52}$N$_7$O$_7$P [M+H]$^+$ calcd.: 642.3738, found: 642.3748.

Example 20: Synthesis of amyl {(5S)-5-[(4-amino-2-oxopyrimidin-1(2H)-yl)methyl]-2-oxido-1,4,2-dioxaphosphinan-2-yl}-L-phenylalaninate (15)

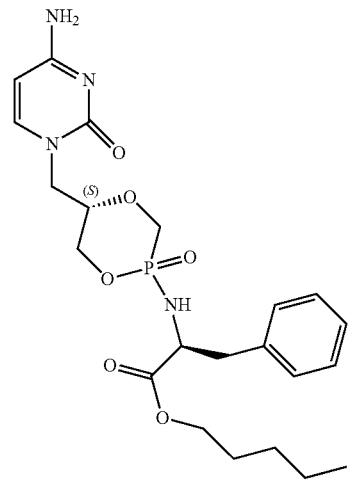

Compound 15 was obtained as a white powder (22 mg, 30%) according to the general procedure, starting from compound 2a (100 mg, 0.15 mmol, Et$_3$N salt), L-phenylalanine amyl ester HCl salt (70 mg, 0.26 mmol), PhOH (61 mg, 0.65 mmol), Et$_3$N (0.15 mL, 1.50 mmol), 2,2'-dithiodipyridine (340 mg, 1.53 mmol), and PPh$_3$ (400 mg, 1.53 mmol) in anhydrous pyridine (5 mL), and in DCM/TCA (6%) (1:1, v/v, 8 mL). The crude residue was purified by column chromatography on silica gel (gradient DCM/MeOH, 15:1, v/v; 10:1, v/v; 8:1). $^1$H NMR (300 MHz, MeOD): δ 7.48-7.20 (m, 6H), 5.86-5.79 (m, 1H), 4.28-3.12 (m, 10H), 3.19-3.12 (m, 1H), 2.97-2.74 (m, 1H), 1.67-1.60 (m, 2H), 1.37-1.31 (m, 4H), 0.95-0.91 (m, 3H); $^{13}$C NMR (75 MHz, MeOD): δ 172.6, 172.3, 166.4, 166.3, 157.2, 146.8, 146.3, 136.8, 129.0, 128.9, 127.8, 126.3, 126.2, 93.9, 93.7, 73.5 (d, $^3J_{C,P}$=4.2 Hz), 73.4 (d, $^3J_{C,P}$=4.9 Hz), 69.7 (d, $^2J_{C,P}$=8.2 Hz), 69.4 (d, $^2J_{C,P}$=7.0 Hz), 66.5, 64.8, 64.6, 63.1, 54.8, 54.4, 48.7, 48.3, 39.6 (d, J=4.9 Hz), 39.4 (d, J=6.0 Hz), 27.6, 27.4, 21.6, 12.6; $^{31}$P NMR (121 MHz, MeOD): δ 17.0, 16.7; HRMS for C$_{22}$H$_{31}$N$_4$O$_6$P [M−H]$^+$ calcd.: 477.1981, found: 477.1904.

Example 21: Synthesis of diamyl ((5S)-5-((4-amino-2-oxopyrimidin-1(2H)-yl)methyl)-2-oxido-1,4,2-dioxaphosphinan-2-yl)-L-glutamate (16)

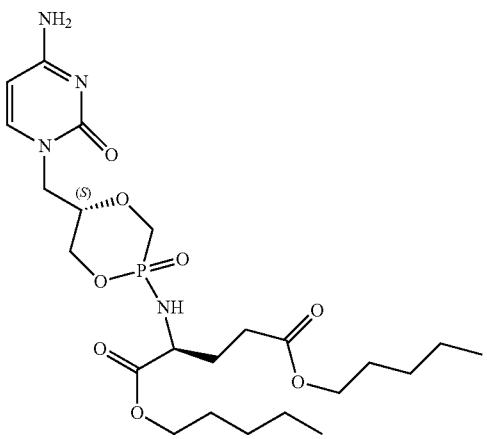

Compound 16 was obtained as a white powder (51 mg, 25%) according to the general procedure, starting from compound 2a (250 mg, 0.38 mmol, Et$_3$N salt), L-glutamic acid amyl ester HCl salt (210 mg, 0.65 mmol), PhOH (61 mg, 0.65 mmol), Et$_3$N (0.15 mL, 1.50 mmol), 2,2'-dithiodipyridine (840 mg, 3.83 mmol), and PPh$_3$ (1.00 g, 3.83 mmol) in anhydrous pyridine (5 mL), and in DCM/TCA (6%) (1:1, v/v, 8 mL). The crude residue was purified by column chromatography on silica gel (gradient DCM/MeOH, 15:1, v/v; 10:1). $^1$H NMR (300 MHz, MeOD): δ 7.54-7.49 (m, 1H), 5.87-5.82 (m, 1H), 4.48-3.61 (m, 12H), 2.54-2.43 (m, 2H), 2.23-2.12 (m, 1H), 2.00-1.80 (m, 1H), 1.69-1.63 (m, 4H), 1.43-1.34 (m, 8H), 0.96-0.92 (m, 6H); $^{13}$C NMR (75 MHz, MeOD): δ 172.8, 172.7, 172.5, 172.4, 166.4, 166.3, 157.2, 146.8, 146.4, 93.9, 93.8, 73.7 (d, $^3J_{C,P}$=4.2 Hz), 73.3 (d, $^3J_{C,P}$=4.9 Hz), 69.9 (d, $^2J_{C,P}$=8.2 Hz), 69.5 (d, $^2J_{C,P}$=6.6 Hz), 66.2, 65.1, 64.9, 64.4, 64.1, 63.3, 52.4, 48.4, 29.6, 29.3, 28.2, 28.1, 27.7, 27.6, 27.5, 27.4, 21.7, 21.6; $^{31}$P NMR (121 MHz, MeOD): δ 17.8, 17.0; HRMS for C$_{23}$H$_{39}$N$_4$O$_8$P [M−H]+ calcd.: 529.2433, found: 529.2426.

Example 22: Synthesis of amyl ((5S)-5-((4-amino-2-oxopyrimidin-1(2H)-yl)methyl)-2-oxido-1,4,2-dioxaphosphinan-2-yl)-L-valinate (17)

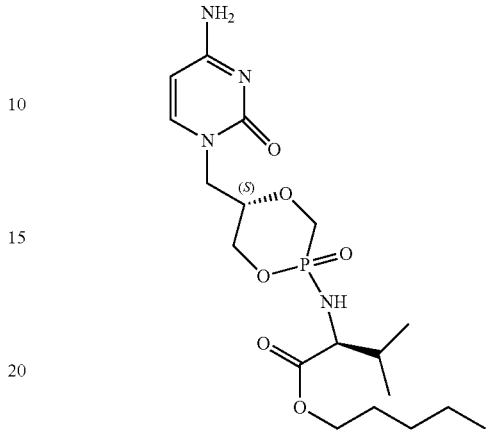

Compound 17 was obtained as a white powder (22 mg, 28%) according to the general procedure, starting from compound 2a (120 mg, 0.18 mmol, Et$_3$N salt), L-valine amyl ester HCl salt (70 mg, 0.31 mmol), PhOH (61 mg, 0.65 mmol), Et$_3$N (0.15 mL, 1.50 mmol), 2,2'-dithiodipyridine (405 mg, 1.80 mmol), and PPh$_3$ (482 mg, 1.80 mmol) in anhydrous pyridine (5 mL), and in DCM/TCA (6%) (1:1, v/v, 8 mL). The crude residue was purified by column chromatography on silica gel (gradient DCM/MeOH, 15:1, v/v; 10:1, v/v; 8:1). $^1$H NMR (300 MHz, MeOD): δ 7.54-7.49 (m, 1H), 5.87-5.82 (m, 1H), 4.47-3.68 (m, 10H), 2.16-2.05 (m, 1H), 1.69-1.65 (m, 2H), 1.41-1.36 (m, 4H), 1.01-0.88 (m, 9H); $^{13}$C NMR (75 MHz, MeOD): δ 172.8, 172.7, 172.5, 166.4, 166.3, 157.3, 157.2, 146.8, 146.4, 93.9, 93.7, 73.7 (d, $^3J_{C,P}$=4.2 Hz), 73.2 (d, $^3J_{C,P}$=5.2 Hz), 69.8 (d, $^2J_{C,P}$=8.2 Hz), 69.5 (d, $^2J_{C,P}$=6.9 Hz), 66.2, 64.8, 64.6, 64.5, 64.4, 63.0, 58.7, 58.5, 48.7, 48.2, 31.1, 31.0, 27.7, 27.5, 21.6, 18.0, 17.9, 16.4, 16.0, 12.6; $^{31}$P NMR (121 MHz, MeOD): δ 17.9, 17.4; HRMS for C$_{18}$H$_{31}$N$_4$O$_6$P [M+H]+ calcd.: 431.2054, found: 431.2035.

Example 23: Synthesis of amyl ((5S)-5-((4-amino-2-oxopyrimidin-1(2H)-yl)methyl)-2-oxido-1,4,2-dioxaphosphinan-2-yl)-L-leucinate (18)

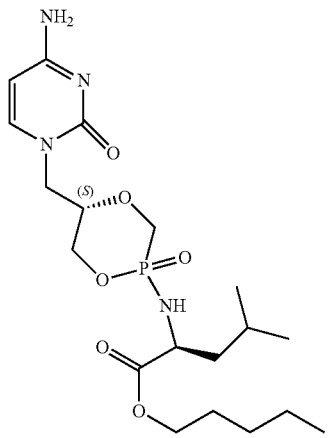

Compound 18 was obtained as a white powder (23 mg, 28%) according to the general procedure, starting from compound 2a (120 mg, 0.18 mmol, Et$_3$N salt), L-leucine amyl ester HCl salt (74 mg, 0.31 mmol), PhOH (61 mg, 0.65 mmol), Et$_3$N (0.15 mL, 1.50 mmol), 2,2'-dithiodipyridine (405 mg, 1.80 mmol), and PPh$_3$ (482 mg, 1.80 mmol) in anhydrous pyridine (5 mL), and in DCM/TCA (6%) (1:1, v/v, 8 mL). The crude residue was purified by column chromatography on silica gel (gradient DCM/MeOH, 15:1, v/v; 10:1, v/v; 8:1). $^1$H NMR (300 MHz, MeOD): δ 7.53-7.49 (m, 1H), 5.86-5.82 (m, 1H), 4.46-3.61 (m, 10H), 1.81-1.53 (m, 5H), 1.41-1.35 (m, 4H), 1.00-0.91 (m, 9H); $^{13}$C NMR (75 MHz, MeOD): δ 173.9, 173.8, 173.5, 166.4, 166.3, 157.3, 157.2, 146.8, 146.4, 93.9, 93.7, 73.7 (d, $^3J_{C,P}$=4.1 Hz), 73.4 (d, $^3J_{C,P}$=5.1 Hz), 69.8 (d, $^2J_{C,P}$=8.2 Hz), 69.4 (d, $^2J_{C,P}$=6.7 Hz), 66.3, 65.2, 64.6, 64.5, 63.4, 51.6, 51.4, 48.7, 48.3, 42.2, 42.1, 42.0, 27.7, 27.6, 27.4, 24.0, 23.9, 21.6, 19.9, 12.6; $^{31}$P NMR (121 MHz, MeOD): δ 17.6, 16.9; HRMS for C$_{19}$H$_{33}$N$_4$O$_6$P [M–H]+ calcd.: 443.2065, found: 443.2058.

Example 24: Synthesis of amyl ((5S)-5-((4-amino-2-oxopyrimidin-1(2H)-yl)methyl)-2-oxido-1,4,2-dioxaphosphinan-2-yl)-L-isoleucinate (19)

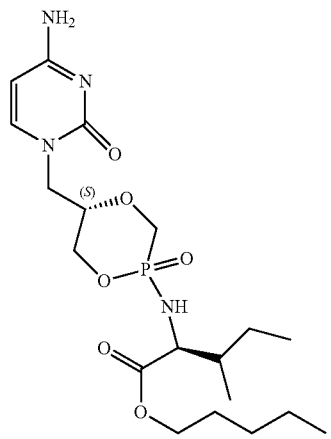

Compound 19 was obtained as a white powder (24 mg, 29%) according to the general procedure, starting from compound 2a (120 mg, 0.18 mmol, Et$_3$N salt), L-isoleucine amyl ester HCl salt (74 mg, 0.31 mmol), PhOH (61 mg, 0.65 mmol), Et$_3$N (0.15 mL, 1.50 mmol), 2,2'-dithiodipyridine (405 mg, 1.80 mmol), and PPh$_3$ (482 mg, 1.80 mmol) in anhydrous pyridine (5 mL), and in DCM/TCA (6%) (1:1, v/v, 8 mL). The crude residue was purified by column chromatography on silica gel (gradient DCM/MeOH, 15:1, v/v; 10:1, v/v; 8:1). $^1$H NMR (300 MHz, CD$_3$CN): δ 7.35-7.33 (m, 1H), 5.91 (s, 2H), 5.73-5.68 (m, 1H), 4.36-3.49 (m, 11H), 1.78-1.59 (m, 3H), 1.50-1.31 (m, 5H), 1.23-1.08 (m, 1H), 0.93-0.83 (m, 9H); $^{13}$C NMR (75 MHz, CD$_3$CN): δ 174.0, 173.9, 173.8, 167.5, 167.4, 157.3, 157.2, 148.2, 147.9, 94.0, 93.9, 74.9 (d, $^3J_{C,P}$=4.3 Hz), 74.6 (d, $^3J_{C,P}$=4.8 Hz), 71.0 (d, $^2J_{C,P}$=8.3 Hz), 70.6 (d, $^2J_{C,P}$=6.6 Hz), 68.0, 66.7, 66.2, 65.8, 64.9, 59.0, 58.9, 39.5, 39.4, 29.0, 28.9, 28.7, 25.2, 22.9, 16.0, 15.9, 14.2, 11.7, 11.6; $^{31}$P NMR (121 MHz, CD$_3$CN): δ 15.1, 14.7; HRMS for C$_{19}$H$_{33}$N$_4$O$_6$P [M+H]+ calcd.: 445.2210, found: 445.2205.

Example 25: Synthesis of diamyl ((5S)-5-((4-amino-2-oxopyrimidin-1(2H)-yl)methyl)-2-oxido-1, 4,2-dioxaphosphinan-2-yl)-D-aspartate (20)

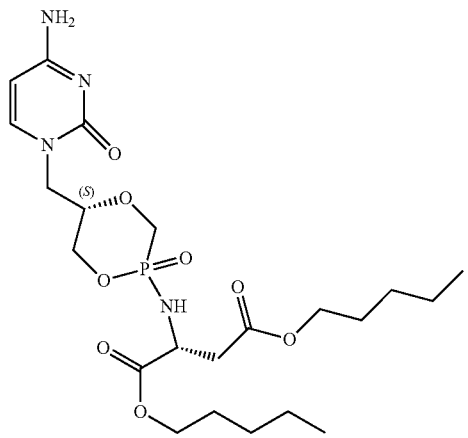

Compound 20 was obtained as a white powder (28 mg, 30%) according to the general procedure, starting from compound 2a (120 mg, 0.18 mmol, Et$_3$N salt), D-aspartic acid amyl ester HCl salt (97 mg, 0.31 mmol), PhOH (61 mg, 0.65 mmol), Et$_3$N (0.15 mL, 1.50 mmol), 2,2'-dithiodipyridine (405 mg, 1.80 mmol), and PPh$_3$ (482 mg, 1.80 mmol) in anhydrous pyridine (5 mL), and in DCM/TCA (6%) (1:1, v/v, 8 mL). The crude residue was purified by column chromatography on silica gel (gradient DCM/MeOH, 15:1, v/v; 10:1, v/v; 8:1). $^1$H NMR (300 MHz, MeOD): δ 7.54-7.51 (m, 1H), 5.87-5.84 (m, 1H), 4.41-3.63 (m, 12H), 2.94-2.78 (m, 2H), 1.73-1.61 (m, 4H), 1.41-1.33 (m, 8H), 0.97-0.91 (m, 6H); $^{13}$C NMR (75 MHz, MeOD): δ 171.9, 171.6, 170.4, 170.3, 166.2, 166.1, 157.0, 146.9, 146.5, 93.9, 93.7, 73.7, 73.6, 70.0 (d, $^2J_{C,P}$=8.2 Hz), 69.7 (d, $^2J_{C,P}$=6.6 Hz), 67.3, 65.5, 65.2, 65.1, 64.4, 63.3, 50.0, 49.2, 48.7, 48.4, 38.1, 37.6, 37.5, 27.7, 27.6, 27.5, 27.4, 21.7, 21.6, 12.6; $^{31}$P NMR (121 MHz, MeOD): δ 17.9, 17.2; HRMS for C$_{22}$H$_{37}$N$_4$O$_8$P [M+H]$^+$ calcd.: 517.2422, found: 517.2418.

Example 26: Antiviral Activity Against Varicella-Zoster Virus, Human Cytomegalovirus and Herpes Simplex Virus 1 and 2

The compounds are evaluated against the following viruses: herpes simplex virus 1 (HSV-1) strain KOS, thymidine kinase-deficient (TK$^-$) HSV-1 KOS strain resistant to ACV (ACV$^r$), herpes simplex virus 2 (HSV-2) strains Lyons and G, varicella-zoster virus (VZV) strain Oka, TK$^-$ VZV strain 07-1, human cytomegalovirus (HCMV) strains AD-169 and Davis. The antiviral assays are based on inhibition of virus-induced cytopathicity (HSV and HCMV) or plaque formation (VZV) in human embryonic lung (HEL) fibroblasts. Confluent cell cultures in microtiter 96-well plates are inoculated with 100 CCID$_{50}$ of virus (1 CCID$_{50}$ being the virus dose to infect 50% of the cell cultures) or with 20 plaque forming units (PFU) (VZV). After 2 hours of adsorption, the viral inoculum is removed and the cultures are further incubated in the presence of varying concentrations of the test compounds. Viral cytopathicity or plaque formation is recorded after 2-3 (HSV), 5 (VZV) or 6-7 (HCMV) days post-infection. Antiviral activity is expressed as the $EC_{50}$ or compound concentration required inhibiting virus-induced cytopathicity or viral plaque formation by 50% (see Tables 1 and 2).

The cytostatic activity measurements are based on the inhibition of cell growth. HEL cells are seeded at a rate of $5 \times 10^3$ cells/well into 96-well microtiter plates and allow proliferating for 24 hours. Then, medium containing different concentrations of the test compounds is added. After 3 days of incubation at 37° C., the cell number is determined with a Coulter counter. The cytostatic concentration is calculated as the $CC_{50}$, or the compound concentration required reducing cell proliferation by 50% relative to the number of cells in the untreated controls. $CC_{50}$ values are estimated from graphic plots of the number of cells (percentage of control) as a function of the concentration of the test compounds. Alternatively, cytotoxicity of the test compounds is expressed as the minimum cytotoxic concentration (MCC) or the compound concentration that causes a microscopically detectable alteration of cell morphology (see Tables 1 and 2).

TABLE 1

Antiviral Activity and Cytotoxicity of the prodrugs against HSV in HEL Cells

| | Antiviral activity $EC_{50}$ (μM)[a] | | | Cytotoxicity | |
|---|---|---|---|---|---|
| | HSV-1 | | | HEL cells | |
| Example # | KOS strain | KOS ACV[r] strain | HSV-2 G strain | MCC[b] | $CC_{50}$[c] |
| 8 | 0.0032 | 0.00073 | 0.0020 | 13.6 | 2.73 |
| 9 | 0.21 | 0.076 | 0.11 | >18.5 | 11.6 |
| 10 | 0.014 | 0.0077 | 0.013 | 19.4 | 33.1 |
| 11 | 2.42 | 1.58 | 3.45 | >19 | >194 |
| 12 | 0.0035 | 0.0015 | 0.0023 | 9.3 | 30.6 |
| 13 | 0.0089 | 0.0057 | 0.011 | 4.11 | 39.6 |
| 14 | 0.020 | 0.010 | 0.017 | 23.5 | 3.40 |
| 15 | 0.0012 | 0.0012 | 0.0025 | 13.2 | 0.52 |
| 16 | 0.0030 | 0.0018 | 0.0019 | 4.40 | 7.76 |
| 17 | 0.0020 | 0.0013 | 0.0019 | 4.27 | 1.62 |
| 18 | 0.0020 | 0.0019 | 0.0027 | 9.96 | 12.0 |
| 19 | 0.0023 | 0.00090 | 0.0028 | 8.57 | 0.60 |
| Acyclovir | 0.47 | >88.8 | 0.34 | >88.8 | >444 |
| Penciclovir | 0.48 | >79.0 | 0.84 | >79.0 | >395 |
| Brivudin | 0.043 | >30.0 | >30.0 | >30.0 | >300 |
| Ganciclovir | 0.057 | >29.5 | 0.051 | >39.2 | >319 |
| Cidofovir | 4.18 | 1.95 | 2.73 | >71.6 | >358 |

[a]Effective concentration required to reduce virus-induced cytopathicity (HSV) by 50%.
[b]Minimum concentration required to cause a microscopically detectable alteration of cell morphology.
[c]Cytotoxic concentration required to reduce cell viability by 50%.

TABLE 2

Antiviral Activity and Cytotoxicity of the prodrugs against VZV and HCMV in HEL Cells

| | Antiviral activity $EC_{50}$ (μM)[a] | | | | Cytotoxicity | |
|---|---|---|---|---|---|---|
| | VZV | | HCMV | | HEL cells | |
| | TK[+] strain | TK[−] | AD-169 | Davis | | |
| Example # | (OKA) | strain | strain | strain | MCC[b] | $CC_{50}$[c] |
| 8 | 0.0014 | 0.0015 | 0.027 | 0.009 | 13.6 | 2.73 |
| 9 | 0.033 | 0.062 | 4.39 | 1.62 | >18.5 | 11.6 |
| 10 | 0.0055 | 0.0063 | 0.012 | 0.019 | 19.4 | 33.1 |
| 11 | 0.81 | 1.24 | 2.68 | 3.53 | >19 | >194 |
| 12 | 0.00052 | 0.0032 | 0.031 | 0.017 | 9.3 | 30.6 |
| 13 | 0.0026 | 0.0040 | 0.032 | 0.029 | 4.11 | 39.6 |
| 14 | 0.0020 | 0.0043 | 0.064 | 0.065 | 23.5 | 3.40 |
| 15 | 0.00058 | 0.00095 | 0.014 | 0.0076 | 13.2 | 0.52 |
| 16 | 0.00057 | 0.0015 | 0.0059 | 0.0048 | 4.40 | 7.76 |
| 17 | 0.00047 | 0.00059 | 0.0057 | 0.0038 | 4.27 | 1.62 |
| 18 | 0.00045 | 0.00054 | 0.007 | 0.0065 | 9.96 | 12.0 |
| 19 | 0.0015 | 0.00095 | 0.10 | 0.072 | 8.57 | 0.60 |
| Acyclovir | 2.84 | 54.8 | ND[d] | ND[d] | >88.8 | >444 |
| Brivudin | 0.053 | 22.1 | ND[d] | ND[d] | >30.0 | >300 |
| Cidofovir | ND[d] | ND[d] | 1.60 | 0.84 | >71.6 | >358 |
| Ganciclovir | ND[d] | ND[d] | 7.40 | 3.31 | >39.2 | >319 |

[a]Effective concentration required to reduce virus-induced cytopathicity (HCMV) or plaque formation (VZV) by 50%.
[b]Minimum concentration required to cause a microscopically detectable alteration of cell morphology.
[c]Cytotoxic concentration required to reduce cell viability by 50%.
[d]Not determined Example 27: Antiviral Activity Against Vaccinia Virus and Human Adeno Virus-2

HEL 299 cells (ATCC® CCL-137) were seeded in Dulbecco's Modified Eagle Medium supplemented with 10% FBS (Hyclone) in 96-well plates, and incubated for 6 days at 37° C. until confluency was reached. Medium was aspirated and replaced by serial dilutions of the test compounds (100 μl per well). One hundred microliters of the virus (Vaccinia virus (strain Lederle, ATCC® VR-118) or human adeno virus-2 (clinical isolate C251085), diluted in DMEM supplemented with 2% FBS to obtain a viral input of 100 CCID50 (1 CCID50 being the virus dose that is able to infect 50% of the cell cultures), was added to each well. Mock-treated cell cultures receiving solely the test compounds were included to determine the cytotoxicity. After 4 days (Vaccinia virus) or 10 days (Adeno virus-2) of incubation at 37° C., microscopy was performed to score the virus-induced cytopathicity.

TABLE 3

Antiviral Activity and Cytotoxicity of the prodrugs against vaccinia virus and adenovirus-2 in HEL Cells

| | Antiviral activity $EC_{50}$ (μM)[a] | | Cytotoxicity |
|---|---|---|---|
| Example # | Vaccinia virus | Adenovirus 2 | MCC[b] |
| 8 | 0.077 | 0.183 | ≥20 |
| 17 | 0.0775 | 0.0435 | ≥0.8 |
| 19 | 0.0425 | 0.0135 | ≥20 |
| Brivudin | 5.8 | ND[c] | >250 |
| Cidofovir | 50 | 10 | >250 |

[a]Effective concentration required to reduce virus-induced cytopathicity by 50%.
[b]Minimum concentration required to cause a microscopically detectable alteration of cell morphology.
[c]ND: not determined.

The invention claimed is:
1. A compound of formula Ia:

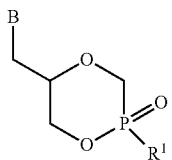

Ia wherein
B is a natural or modified nucleobase
$R^1$ has the general formula II

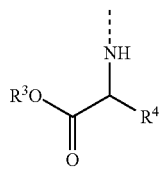

II wherein
$R^3$ is selected from the group consisting of aryl, heteroaryl, $C_1$-$C_{10}$ alkyl, $C_3$-$C_8$-cycloalkyl, $C_3$-$C_8$-cycloalkyl-alkyl, aryl($C_1$-$C_6$)alkyl, $C_2$-$C_{10}$ alkenyl, $C_2$-$C_{10}$ alkynyl, hydroxyl $C_1$-$C_{10}$ alkyl, halo $C_1$-$C_{10}$ alkyl, and alkoxyalkyl;
$R^4$ is X—$COOR^5$;
wherein X is aryl, heteroaryl, $C_1$-$C_{10}$ alkyl, $C_2$-$C_{10}$ alkenyl, $C_2$-$C_{10}$ alkynyl, or $C_3$-$C_8$-cycloalkyl, and wherein said aryl, heteroaryl, $C_1$-$C_{10}$ alkyl, $C_2$-$C_{10}$ alkenyl, $C_2$-$C_{10}$ alkynyl, $C_3$-$C_8$-cycloalkyl optionally contains one or more functions, atoms or radicals independently selected from the group consisting of halogen, halo-alkyl, cyano, $C_1$-$C_7$ alkoxy; and
wherein $R^5$ is selected from the group consisting of aryl, heteroaryl, $C_1$-$C_{10}$ alkyl, $C_3$-$C_8$-cycloalkyl, $C_3$-$C_8$cycloalkyl-alkyl, aryl($C_1$-$C_6$)alkyl, $C_2$-$C_{10}$ alkenyl, $C_2$-$C_{10}$ alkynyl, hydroxyl $C_1$-$C_{10}$ alkyl, halo $C_1$-$C_{10}$ alkyl, and alkoxyalkyl;
and/or a pharmaceutical acceptable addition salt thereof and/or a stereoisomer thereof and/or a solvate thereof.

2. The compound according to claim 1, wherein B is selected from the group of adenine, thymine, cytosine and guanine.

3. The compound according to claim 1, wherein $R^3$ is selected from $C_1$-$C_{10}$ alkyl.

4. The compound according to claim 1, wherein X is $C_1$-$C_{10}$ alkyl; and $R^5$ is $C_1$-$C_{10}$ alkyl.

5. A compound selected from the group consisting of Diamyl {(5S)-5-[(6-amino-9H-purin-9-yl)methyl]-2-oxido-1,4,2-dioxaphosphinan-2-yl}-L-aspartate; Diamyl {(5R)-5-[(6-amino-9H-purin-9-yl)methyl]-2-oxido-1,4,2-dioxaphosphinan-2-yl}-L-aspartate; Diamyl {(5S)-5-[(4-amino-2-oxopyrimidin-1(2H)-yl)methyl]-2-oxido-1,4,2-dioxaphosphinan-2-yl}-L-aspartate; diamyl {(5R)-5-[(4-amino-2-oxopyrimidin-1(2H)-yl)methyl]-2-oxido-1,4,2-dioxaphosphinan-2-yl}-L-aspartate; Amyl ((5S)-5-((6-amino-9H-purin-9-yl)methyl)-2-oxido-1,4,2-dioxaphosphinan-2-yl)-L-phenylalaninate; Amyl ((5S)-5-((6-amino-9H-purin-9-yl)methyl)-2-oxido-1,4,2-dioxaphosphinan-2-yl)-L-methioninate; Amyl ((5S)-5-((6-amino-9H-purin-9-yl)methyl)-2-oxido-1,4,2-dioxaphosphinan-2-yl)-L-alaninate; Diamyl {(5S)-5-[(6-amino-9H-purin-9-yl)methyl]-2-oxido-1,4,2-dioxaphosphinan-2-yl}-L-glutamate; Amyl {(5S)-5-[(6-amino-9H-purin-9-yl)methyl]-2-oxido-1,4,2-dioxaphosphinan-2-yl}-L-valinate; Amyl {(5S)-5-[(6-amino-9H-purin-9-yl)methyl]-2-oxido-1,4,2-dioxaphosphinan-2-yl}-L-leucinate; Amyl {(5S)-5-[(6-amino-9H-purin-9-yl)methyl]-2-oxido-1,4,2-dioxaphosphinan-2-yl}-L-isoleucinate; diamyl 2,2'-((((((S)-1-(6-amino-9H-purin-9-yl)-3-hydroxypropan-2-yl)oxy)methyl)phosphoryl)bis(azanediyl))(2S,2'S)-bis(3-methylbutanoate); amyl {(5S)-5-[(4-amino-2-oxopyrimidin-1(2H)-yl)methyl]-2-oxido-1,4,2-dioxaphosphinan-2-yl}-L-phenylalaninate; diamyl ((5S)-5-((4-amino-2-oxopyrimidin-1(2H)-yl)methyl)-2-oxido-1,4,2-dioxaphosphinan-2-yl)-L-glutamate; amyl ((5S)-5-((4-amino-2-oxopyrimidin-1(2H)-yl)methyl)-2-oxido-1,4,2-dioxaphosphinan-2-yl)-L-valinate; amyl ((5S)-5-((4-amino-2-oxopyrimidin-1(2H)-yl)methyl)-2-oxido-1,4,2-dioxaphosphinan-2-yl)-L leucinate; amyl ((5S)-5-((4-amino-2-oxopyrimidin-1(2H)-yl)methyl)-2-oxido-1,4,2-dioxaphosphinan-2-yl)-L-isoleucinate; and diamyl ((5S)-5-((4-amino-2-oxopyrimidin-1(2H)-yl)methyl)-2-oxido-1,4,2-dioxaphosphinan-2-yl)-D-aspartate.

6. A pharmaceutical composition comprising a therapeutically effective amount of a compound according to claim 1, and one or more pharmaceutically acceptable excipients.

7. The pharmaceutical composition according to claim 6, further comprising one or more biologically active drugs being selected from the group consisting of antiviral drugs and anti-proliferative drugs.

8. A method of treatment of a viral infection in an animal, mammal or human, comprising the administration of a therapeutically effective amount of a compound according to claim 1, optionally in combination with one or more pharmaceutically acceptable excipients, to the animal, mammal or human.

9. The method according to claim 8, wherein said viral infection is an infection selected from the group consisting of hepatitis B virus (HBV), human immunodeficiency virus (HIV), varicella-zoster virus (VZV), cytomegalovirus (CMV), vaccinia virus (VV), herpes simplex virus (HSV), BK virus, Epstein-barr virus (EBV), papillomavirus, Monkeypox virus, Cowpox virus, hepatitis C virus (HCV), respiratory syncytial virus (RSV), dengue virus, influenza virus, adenovirus, parainfluenza virus and rhinovirus.

10. A method of treatment of a viral infection in an animal, mammal or human, comprising the administration of a therapeutically effective amount of a compound according to claim 5, optionally in combination with one or more pharmaceutically acceptable excipients, to the animal, mammal or human.

11. The method according to claim 10, wherein said viral infection is an infection selected from the group consisting of hepatitis B virus (HBV), human immunodeficiency virus (HIV), varicella-zoster virus (VZV), cytomegalovirus (CMV), vaccinia virus (VV), herpes simplex virus (HSV), BK virus, Epstein-barr virus (EBV), papillomavirus, Monkeypox virus, Cowpox virus, hepatitis C virus (HCV), respiratory syncytial virus (RSV), dengue virus, influenza virus, adenovirus, parainfluenza virus and rhinovirus.

12. A pharmaceutical composition comprising a therapeutically effective amount of a compound according to claim 5, and one or more pharmaceutically acceptable excipients.

* * * * *